(12) United States Patent
Bachmann et al.

(10) Patent No.: US 10,766,943 B2
(45) Date of Patent: Sep. 8, 2020

(54) UNIVERSAL CHIMERIC ANTIGEN EXPRESSING IMMUNE CELLS FOR TARGETING OF DIVERSE MULTIPLE ANTIGENS AND METHOD OF MANUFACTURING THE SAME AND USE OF THE SAME FOR TREATMENT OF CANCER, INFECTIONS AND AUTOIMMUNE DISORDERS

(71) Applicant: GEMoaB Monoclonals GmbH, Dresden (DE)

(72) Inventors: Michael Bachmann, Kelkheim (DE); Armin Ehninger, Dresden (DE)

(73) Assignee: GEMoaB Monoclonals GmbH, Dresden (DE)

( * ) Notice: Subject to any disclaimer, the term of this patent is extended or adjusted under 35 U.S.C. 154(b) by 0 days.

(21) Appl. No.: 16/513,672

(22) Filed: Jul. 16, 2019

(65) Prior Publication Data

US 2019/0352370 A1  Nov. 21, 2019

Related U.S. Application Data

(63) Continuation of application No. 15/504,012, filed as application No. PCT/EP2015/069527 on Aug. 26, 2015.

(30) Foreign Application Priority Data

Aug. 29, 2014  (EP) .................................... 14182945

(51) Int. Cl.
| | | |
|---|---|---|
| A61K 39/00 | (2006.01) |
| C07K 14/725 | (2006.01) |
| C07K 16/18 | (2006.01) |
| A61K 35/17 | (2015.01) |

(52) U.S. Cl.
CPC .......... C07K 14/7051 (2013.01); C07K 16/18 (2013.01); A61K 35/17 (2013.01); A61K 2039/505 (2013.01); C07K 2317/34 (2013.01); C07K 2317/622 (2013.01); C07K 2319/02 (2013.01); C07K 2319/03 (2013.01); C07K 2319/33 (2013.01)

(58) Field of Classification Search
CPC ............................................... A61K 2039/505
See application file for complete search history.

(56) References Cited

U.S. PATENT DOCUMENTS

| | | |
|---|---|---|
| 5,843,728 A | 12/1998 | Seed et al. |
| 5,912,170 A | 6/1999 | Seed et al. |
| 6,410,014 B1 | 6/2002 | Seed et al. |
| 7,049,136 B2 | 5/2006 | Seed et al. |
| 7,074,403 B1 | 7/2006 | Goldenberg et al. |
| 7,235,641 B2 | 6/2007 | Kufer et al. |
| 7,435,803 B2 | 10/2008 | Hansen et al. |
| 7,446,190 B2 | 11/2008 | Sadelain et al. |
| 7,462,352 B2 | 12/2008 | Hansen et al. |
| 7,572,772 B2 | 8/2009 | Linsley et al. |
| 8,399,645 B2 | 3/2013 | Campana et al. |
| 8,624,001 B1 | 1/2014 | Hansen et al. |
| 8,679,492 B2 | 3/2014 | Blein et al. |
| 8,709,421 B2 | 4/2014 | Heiss et al. |
| 8,852,551 B2 | 10/2014 | Jordan |
| 8,926,976 B2 | 1/2015 | Corbin et al. |
| 9,573,988 B2 | 2/2017 | Brogdon et al. |
| 9,657,105 B2 | 5/2017 | Forman et al. |
| 9,815,901 B2 | 11/2017 | Brogdon et al. |
| 10,144,770 B2 | 12/2018 | Campana et al. |
| 2012/0251554 A1 | 10/2012 | Bachmann et al. |
| 2018/0105595 A1 | 4/2018 | Wang et al. |

FOREIGN PATENT DOCUMENTS

| | | |
|---|---|---|
| WO | 1986/004093 A1 | 7/1986 |
| WO | 1988/09932 A1 | 12/1988 |
| WO | 1997/024373 A1 | 10/1997 |
| WO | 2002/077029 A2 | 10/2002 |
| WO | 2007/043103 A1 | 4/2007 |
| WO | WO 2011036183 A2 | 3/2011 |
| WO | WO 2011036183 A3 | 3/2011 |
| WO | 2011/156860 A1 | 12/2011 |
| WO | 2012/017069 A1 | 2/2012 |
| WO | 2012/017082 A2 | 2/2012 |
| WO | 2012/020046 A1 | 2/2012 |
| WO | 2012/082841 A2 | 6/2012 |
| WO | 2013/001065 A1 | 1/2013 |
| WO | 2013/044225 A1 | 3/2013 |
| WO | 2013/074916 | 5/2013 |
| WO | 2013/126712 | 8/2013 |
| WO | 2013/151672 A2 | 10/2013 |
| WO | 2013/173820 A2 | 11/2013 |
| WO | 2014/012001 A2 | 1/2014 |
| WO | 2014/100615 A1 | 6/2014 |
| WO | 2014/127261 A1 | 8/2014 |

(Continued)

OTHER PUBLICATIONS

Ehninger et al. (Blood Cancer J. Jun. 13, 2014;4:e218; pp. 1-10).*
Maher et al. Human T-lymphocyte cytotoxicity and proliferation directed by a single chimeric TCRzeta / CD28receptor. Nat. Biotechnol. Jan. 2002; 20(1)10:70-5.
Krause et al. Antigen-dependent CD28 Signaling Selectively Enhances Survival and Proliferation in Genetically Modified Activated Human Primary T Lymphocytes. J. Exp. Med. Aug. 17, 1998; 188(4):619-26.

(Continued)

*Primary Examiner* — Stephen L Rawlings
(74) *Attorney, Agent, or Firm* — FisherBroyles, LLP; Andrew K. Gonsalves, Esq.

(57) ABSTRACT

The present invention relates to immune cell-based anti-cancer therapeutics and methods of using the therapeutics in the treatment of cancer.

9 Claims, 11 Drawing Sheets

Specification includes a Sequence Listing.

(56) References Cited

FOREIGN PATENT DOCUMENTS

| WO | 2014/130635 A1 | 8/2014 |
| WO | 2015/057834 A1 | 4/2015 |
| WO | 2015/057852 A1 | 4/2015 |
| WO | 2015/140268 A1 | 9/2015 |
| WO | 2015/143224 A1 | 9/2015 |
| WO | 2015/197016 A1 | 12/2015 |
| WO | 2016/030414 | 3/2016 |
| WO | WO 2016168766 A1 | 10/2016 |
| WO | WO 2017091546 A1 | 6/2017 |

OTHER PUBLICATIONS

Nguyen et al. Identification of a murine CD28 dileucine motif that suppresses single-chain chimeric T-cell receptor expression and function. Blood. Dec. 15, 2003; 102(13); 4320-5. Epub Aug. 28, 2003.

Cartellieri et al. Switching CAR T cells on and off: a novel modular platform for retargeting of T cells to AML blasts. Blood Cancer J. Aug. 12, 2016; 6(8): e458. doi: 10.1038/bcj.2016.61.

Zhong et al. Chimeric antigen receptors combining 4-1BB and CD28 signaling domains augment Pl3kinase/AKT/Bcl-XL activation and CD8+ T cell-mediated tumor eradication. Mol. Ther. Feb. 2010; 18(2): 413-20. doi: 10.1038/mt.2009.210. Epub Sep. 22, 2009.

Arndt et al. Simultaneous targeting of prostate stem cell antigen and prostate-specific membrane antigen improves the killing of prostate cancer cells using a novel modular T cell-retargeting system. Prostate. Sep. 2014;74(13):1335-46.doi: 10.1002/pros.22850. Epub Jul. 22, 2014.

Feldmann et al. Novel humanized and highly efficient bispecific antibodies mediate killing of prostate stem cell antigen-expressing tumor cells by CD8+ and CD4+ T cells. J Immunol. Sep. 15, 2012;189(6):3249-59. doi: 10A049/immunol.1200341. Epub Aug. 8, 2012.

Koristka et al. Retargeting of human regulatory T cells by single-chain bispecific antibodies. J Immunol. Feb. 1, 2012;188(3):1551-8. doi: 10.4049/jimmunol.1101760. Epub Dec. 19, 2011.

Kristiansen, G. Diagnostic and prognostic molecular biomarkers for prostate cancer. Histopathology. Jan. 2012;60(1):125-41. doi: 10.1111/j.1365-2559.2011.04083.x.

Stamova et al. Unexpected recombinations in single chain bispecific anti-CD3-anti-CD33 antibodies can be avoided by a novel linker module. Mol Immunol. Dec. 2011;49(3):474-82. doi: 10.1016/j.molimm.2011.09.019. Epub Oct. 19, 2011.

Feldmann et al. Retargeting of T cells to prostate stem cell antigen expressing tumor cells: comparison of different antibody formats. Prostate. Jun. 15, 2011;71(9):998-1011. doi: 10.1002/pros.21315. Epub Dec. 28, 2010.

International Search Report and Written Opinion dated Oct. 12, 2015 issued in PCT/EP2015/069527; 9 pages.

Arndt et al., 2014, "Costimulation improves the killing capability of T cells redirected to tumor cells expressing low levels of CD33: description of a novel modular targeting system", Leukemia, 28:59-69.

Evans et al., 1985, "Isolation of monoclonal antibodies specific for human c-myc proto-oncogene product", Mol. Cell Biol., 5(12):3610-6.

Park et al., 2010, "Adoptive immunotherapy for B-cell malignancies with autologous chimeric antigen receptor modified tumor targeted T cells", Discovery Medicine, 9(47):277-288.

Terpe, K., 2003, "Overview of tag protein fusions: from molecular and biochemical fundamentals to commercial systems", Appl. Nicrobiol. Biotechnol., 60(5):523-33.

Canadian Intellectual Property Office, Examination Report dated Dec. 7, 2017 for Canadian Patent Application No. CA 2,953,276; 4 pages.

Bippes et al., 2011 A Novel Modular Antigen Delivery System for Immuno Targeting of Human 6-sulfo LacNAc-Positive Blood Dendritic Cells (SlanDCs), PLoS One., 6(1):e16315; pp. 1-5.

Evans et al., "Isolation of monoclonal antibodies specific for human c-myc proto-oncogene product," *Mol. Cell. Biol.*, 5(12):3610-3616 (1985).

Terpe et al., "Overview of tag protein fusions: from molecular and biochemical fundamentals to commercial systems," *Appl. Microbiol. Biotechnol.*, 60(5):523-533 (2003).

Arndt et al., *Blood*, 118:1528, pp. 1-7 (2011).

Bippes et al., "A novel modular antigen delivery system for immuno targeting of human 6-sulfo LacNAc-positive blood dendritic cells (SlanDCs)," *PLoS One*, 6(1):e16315, pp. 1-15 (2011).

Tettamanti et al., "Targeting of acute myeloid leukaemia by cytokine-induced killer cells redirected with a novel CD123-specific chimeric antigen receptor," *British Journal of Haematology*, 161:389-401 (2013).

Arndt et al., "Enhancing the efficacy and specificity of antibody-based T cell retargeting strategies against hematolgical malignancies," *Blood*, 122:930 (2013).

Hanawa et al., "A novel costimulatory signaling in human T lymphocytes by a splice variant of CD28," Blood, 99(6):2138-2145 (2002).

\* cited by examiner

UNIVERSAL CHIMERIC ANTIGEN EXPRESSING IMMUNE CELLS FOR TARGETING OF DIVERSE MULTIPLE ANTIGENS AND METHOD OF MANUFACTURING THE SAME AND USE OF THE SAME FOR TREATMENT OF CANCER, INFECTIONS AND AUTOIMMUNE DISORDERS

RELATED APPLICATIONS

This application is a continuation of U.S. application Ser. No. 15/504,012, filed Feb. 14, 2017, which is a 371 national stage application of International Application No. PCT/EP2015/069527 filed Aug. 26, 2015, which claims the benefit to EP Application No. 14182945.7, filed Aug. 29, 2014, each of which is incorporated herein by reference in its entirety.

SEQUENCE LISTING

This application incorporates by reference a Sequence Listing submitted with this application as text file entitled "2019-07-16_SequenceListing_6385018US2.TXT" created on Jul. 16, 2019 and having a size of 54,979 bytes.

TECHNICAL FIELD

The present invention relates to immune cell-based therapeutics and methods of using the therapeutics in the treatment of cancer, infections and autoimmune disorders.

BACKGROUND OF INVENTION

Chimeric antigen receptors (CARs) are artificial receptors consisting of a binding moiety which provides the antigen-specificity and one or several signaling chains derived from immune receptors (Cartellieri et al., J. Biomed. Biotechnol. doi: 10.1155/2010/956304 (2010)). These two principal CAR domains are connected by a linking peptide chain including a transmembrane domain, which anchors the CAR in the cellular plasma membrane. Immune cells, in particular T and NK lymphocytes, can be genetically modified to express CARs inserted into their plasma membrane. If such a CAR modified immune cell encounters other cells or tissue structures expressing or being decorated with the appropriate target of the CAR binding moiety, upon binding of the CAR binding moiety to the target antigen the CAR modified immune cell is cross-linked to the target. Cross-linking leads to an induction of signal pathways via the CAR signaling chains, which will change the biologic properties of the CAR engrafted immune cell. For example, CAR triggering in effector CD4+ and CD8+ T cells will activate typical effector functions like secretion of lytic compounds and cytokines which will eventually lead to the killing of the respective target cell. The adoptive transfer of immune cells engineered with chimeric antigen receptors (CARs) is currently considered as a highly promising therapeutic option for treatment of otherwise incurable malignant, infectious or autoimmune diseases. First clinical trials demonstrated both the safety and the feasibility of this treatment strategy (Lamers et al. J. Clin. Oncol. 24 e20-e22 (2006), Kershaw et al. Clin. Cancer Res. 12 6106-61 15 (2006)). In recent ongoing trials, a majority of patients suffering from late-stage tumors of B cell origin showed complete or at least partial response to a treatment with autologous T cells equipped with a CD19-specific CAR, which lasted for several months (Brentjens et al. Blood. 118 4817-4828 (2011), Sci. Transl. Med. 20(5) doi: 10.1126/scitranslmed.3005930 (2013), Kalos et al. 2011 Sci. Transl. Med. 3(95) doi: 10.1126/scitranslmed. 3002842, Grupp et al. N. Engl. J. Med. 368: 1509-1518 (2013)).

However, the conventional CAR technology comes along with a number of critical issues which need to be solved before this treatment modality can be widely applied for clinical treatments. First of all, several safety issues have to be addressed. So far, immune responses of T cells engineered with conventional CARs are difficult to control after infusion into the patient Especially unexpected target gene expression on healthy tissue may provoke a rapid and rigorous immune reaction of engineered T cells against healthy cells, which can cause severe side effects (Lamers et al. J. Clin. Oncol. 24 e20-e22 (2006), Morgan et al. Mol. Ther. 18: p. 843-851 (2010). Another drawback of conventional CAR technology is the restriction of engineered T cell retargeting to a single antigen. Such a monotherapeutic approach implies the risk for development of tumor escape variants, which have lost the target antigen during treatment. The emergence of tumor escape variants under conventional CAR T cell therapy after several months was already observed in clinical trials, (Grupp et al. N. Engl. J. Med. 368: 1509-1518 (2013)).

WO 2012082841 A2 discloses universal anti-tag chimeric antigen receptor-expressing T cells and methods of treating cell related disorders, e.g. cancer.

In addition WO 2013044225 A1 discloses a universal immune receptor expressed by T cells for the targeting of diverse and multiple antigens.

Both methods describe the use of modified T cells expressing universal anti-tag immune receptors. These T cells can be redirected to disease-related cell surface antigens by additionally applying modules binding these surface antigens and carrying the respective tag. The problem arising from the aforesaid methods is that a redirection of the genetically modified T cells using exogenous tags is likely to be immunogenic, which will put patients in danger and negatively affect efficacy of treatment.

Therefore, it is an object of the present invention to provide a genetically modified immune cell that allows a redirection against diverse disorders in a safe and efficient manner using endogenous tags based on nuclear proteins. It is a further object of the present invention to provide a method of treatment of diverse cell related disorders, wherein the length and intensity of treatment is adjustable in a simple manner.

SUMMARY OF INVENTION

The present invention provides an universal, modular, anti-tag chimeric antigen receptor (UniCAR) system that allows a retargeting of UniCAR engrafted immune cells against multiple antigens. The system uses a gene therapy platform to generate immune cells capable of recognizing various antigens and that have broad and valuable clinical implications for the use of immune cell-based therapies, in particular T- and NK-cell based therapies.

In a first aspect the present invention provides an isolated nucleic acid sequence encoding a universal chimeric antigen receptor, wherein the receptor comprises three domains, wherein the first domain is a tag-binding domain, the second domain is a linking peptide chain including an extracellular hinge and a transmembrane domain and the third domain is a signal transduction domain, wherein the tag-binding domain binds to a tag derived from any human nuclear protein. In particular suitable tags are peptide sequences from nuclear antigens, which cannot be accessed and bound by the corresponding tag-binding domain in the context of the native protein under physiological conditions. In addition, the peptide sequence should not be the target of autoantibodies in autoimmune patients, thus making it unlikely that the tag is immunogenic in the context of the universal chimeric receptor. An optional fourth domain is a short peptide linker in the extracellular portion of UniCARs, which forms a linear epitope for a monoclonal antibody (mab) specifically binding to the fourth domain. This additional domain is not required for functionality of the UniCAR system, but may add additional clinical benefit to the invention. Preferably the present invention provides an isolated nucleic acid sequence encoding a universal chimeric antigen receptor according to the present invention, wherein the nucleic acid sequence encodes for an artificial chimeric fusion protein and wherein the nucleic acid sequence is provided as cDNA.

In a further aspect the present invention provides a target module composed of a binding moiety specific for a certain human cell surface protein or protein complex and a tag, wherein the tag is derived from any human nuclear protein.

In a further aspect the present invention provides a nucleic acid encoding a target module according to the present invention. Preferably the present invention provides an isolated nucleic acid sequence encoding a target module according to the present invention, wherein the isolated nucleic is provided as cDNA.

In a further aspect the present invention provides a cell comprising a nucleic acid encoding an universal chimeric antigen receptor according to the present invention comprising three domains, wherein the first domain is a tag-binding domain, the second domain is a linking peptide chain including an extracellular hinge and a transmembrane domain and the third domain is a signal transduction domain and wherein the tag-binding domain binds to a tag derived from any human nuclear protein.

In a further aspect the present invention provides a vector comprising a nucleic acid encoding a universal chimeric antigen receptor according to the present invention, wherein the universal chimeric antigen receptor comprises three domains, wherein the first domain is a tag-binding domain, the second domain is a linking peptide chain including an extracellular hinge and a transmembrane domain and the third domain is a signal transduction domain, wherein the tag-binding domain binds to a tag derived from any human nuclear protein.

In a further aspect the present invention provides a kit comprising a vector according to the present invention comprising a nucleic acid sequence encoding a universal chimeric antigen receptor according to the present invention and a target module according to the present invention and/or a vector encoding an isolated nucleic acid sequence encoding a target module according to the present invention.

The invention encompasses moreover a pharmaceutical composition that contains cells and target modules according to the invention in association with a pharmaceutically acceptable dilution agent or carrier. Preferably, the pharmaceutical composition is present in a form suitable for intravenous administration.

Preferably, the composition comprises cells comprising a nucleic acid encoding a universal chimeric antigen receptor according to the present invention and target modules according to the present invention.

The pharmaceutical composition according to the invention comprises various administration forms. The pharmaceutical compositions are preferably administered parenterally, particularly preferred intravenously. In one embodiment of the invention, the parenteral pharmaceutical composition exists in an administration form that is suitable for injection. Particularly preferred compositions are therefore solutions, emulsions, or suspensions of the cell and target module that are present in a pharmaceutically acceptable dilution agent or carrier.

As a carrier, preferably water, buffered water, 0.4% saline solution, 0.3% glycine and similar solvents are used. The solutions are sterile. The pharmaceutical compositions are sterilized by conventional well-known techniques. The compositions contain preferably pharmaceutically acceptable excipients, for example, those that are required in order to provide approximately physiological conditions and/or to increase the stability of the target modul, such as agents for adjusting the pH value and buffering agents, agents for adjusting the toxicity and the like, preferably selected from sodium acetate, sodium chloride, potassium chloride, calcium chloride and sodium lactate. The concentrations of the target moduls according to the invention in these formulations, depending on the application, are variable; they are preferably less than 0.01% by weight, preferably at least 0.1% by weight, further preferred between 1 and 5% by weight and they are selected primarily on the basis of fluid volumes, viscosity etc. or in compliance with the respective administration mode.

Pharmaceutical compositions must be sterile and stable under the manufacturing and storage conditions. The composition can be formulated as a solution, microemulsion, dispersion, in liposomes or in other ordered structures that are suitable for this purpose and know by the artesian.

The cells and target module according to the invention are preferably introduced into a composition that is suitable for parenteral administration. Preferably, the pharmaceutical composition is an injectable buffered solution that contains between 0.001 to 500 mg/ml of antibody, especially preferred between 0.001 to 250 mg/ml of target modul, in particular together with 1 to 500 mmol/l (mM) of a buffer. The injectable solution can be present in liquid form. The buffer can be preferably histidine (preferably 1 to 50 mM, especially preferred 5 to 10 mM) at a pH value of 5.0 to 7.0 (especially preferred at a pH of 6.0).

Other suitable buffers encompass, but are explicitly not limited to, sodium sucdnate, sodium citrate, sodium phosphate, or potassium phosphate. Preferably, sodium chloride between 0 to 300 mM, especially preferred 150 mM, is used for a liquid administration form. In liquid administration forms, stabilizers are preferably used, especially preferred between 1 to 50 mM of L-methionine (preferably between 5 and 10 mM).

A typical dose-rate delivered per m2 per day is between 1 µg to 1000 mg, preferably 10 µg to 1 mg, with dosages administered one or more times per day or week or continuously over a period of several weeks.

In a further aspect the invention provides the use of cells according to the present invention comprising a nucleic acid encoding a universal chimeric antigen receptor according to the present invention and target modules according to the present invention for stimulating a universal chimeric antigen receptor mediated immune response in mammals. Preferably the invention provides the use of cells according to the present invention comprising a nucleic acid encoding a universal chimeric antigen receptor according to the present invention and target modules according to the present invention as a medication, more preferably as a medication for treatment of cancer or an autoimmune disease. An autoimmune disease arises from an abnormal immune response of the body against substances and tissues normally present in the body (autoimmunity).

The invention comprises further the use of cells and target modules according to the invention for preparing a medication for therapeutic and/or diagnostic use in case of cancer or an autoimmune disease.

The invention also encompasses a method for treatment of a human having cancer or an autoimmune disease by administration of cells and target modules according to the invention.

For therapeutic applications, a sterile pharmaceutical composition, containing a pharmacologically effective quantity of cells and target module according to the invention, is administered to a patient in order to treat the aforementioned illnesses.

The invention will be explained in more detail with the aid of the following figures and embodiments without limiting the invention to them.

DETAILED DESCRIPTION OF FIGURES

FIG. 1 depicts a schematic illustration of the universal chimeric antigen receptor (UniCAR), FIG. 2 shows a schematic illustration of the universal chimeric antigen receptor (UniCAR) platform for antigen-specific immune cell retargeting, FIG. 3 shows a schematic map of the lentiviral vector pI_VX-EF1a-IRES-ZsGreen1, FIG. 4 shows a schematic map of the lentiviral packaging plasmid psPAX2, FIG. 5 shows a schematic map of the envelope plasmid pMD2.G, FIG. 6 depicts diagrams showing UniCAR surface expression detected by using a monoclonal antibody directed against the optional $4^{th}$ domain, FIG. 7A-7D shows diagrams of effector functions of UniCAR engineered T cells against tumor cells expressing the prostate stem cell antigen and prostate membrane antigen.

DETAILED DESCRIPTION OF INVENTION

Effector Cells

The effector cells used in the methods of the present invention may be autologous, syngeneic or allogeneic, with the selection dependent on the disease to be treated and the means available to do so. Suitable populations of effector cells that may be used in the methods include any immune cells with cytolytic, phagocytic or immunosuppressive activity, such as T cells, including regulatory T cells, NK cells and macrophages. In one aspect, effector cells are from a certain HLA background and utilized in an autologous or allogeneic system. Effector cells can be isolated from any source, including from a tumor explant of the subject being treated or intratumoral cells of the subject being treated. In the following, the term "effector cell" refers to any kind of aforementioned immune cells genetically altered to express UniCARs on their cell surface.

Universal Chimeric Antigen Receptor (UniCAR)

The UniCAR expressed by effector cells used in the methods of the present invention allows for a modular, highly flexible and tightly controllable retargeting of UniCAR expressing immune cells in an antigen-specific manner. The sole requirements for the UniCARs used in the methods are (i) that the UniCAR has binding specificity for a particular tag that can be conjugated to a target module, which in turn binds to a cellular surface protein or an extracellular structure, and (ii) that immune cells can be engineered to express the UniCAR.

Figure 1:
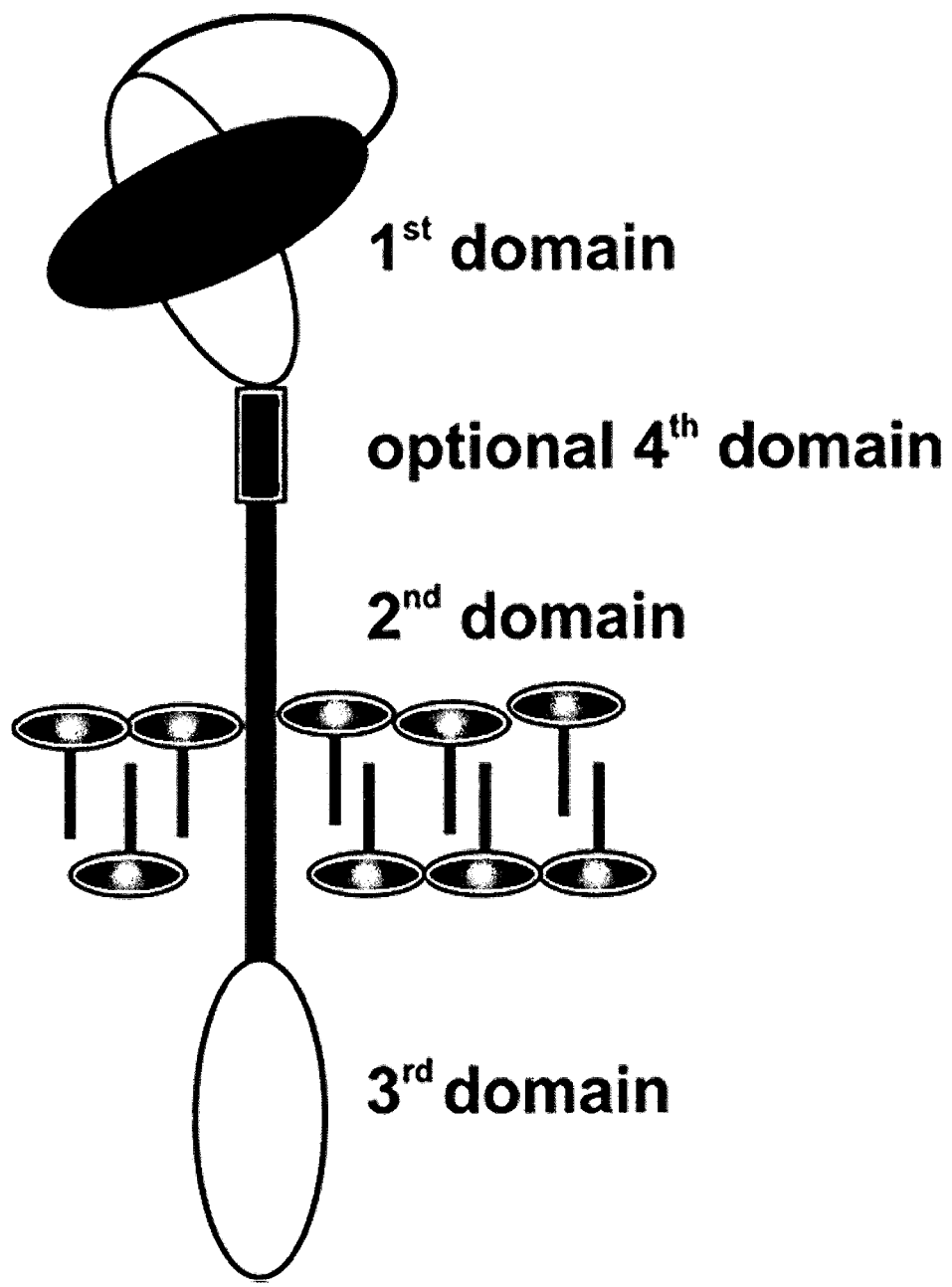
Figure 2:
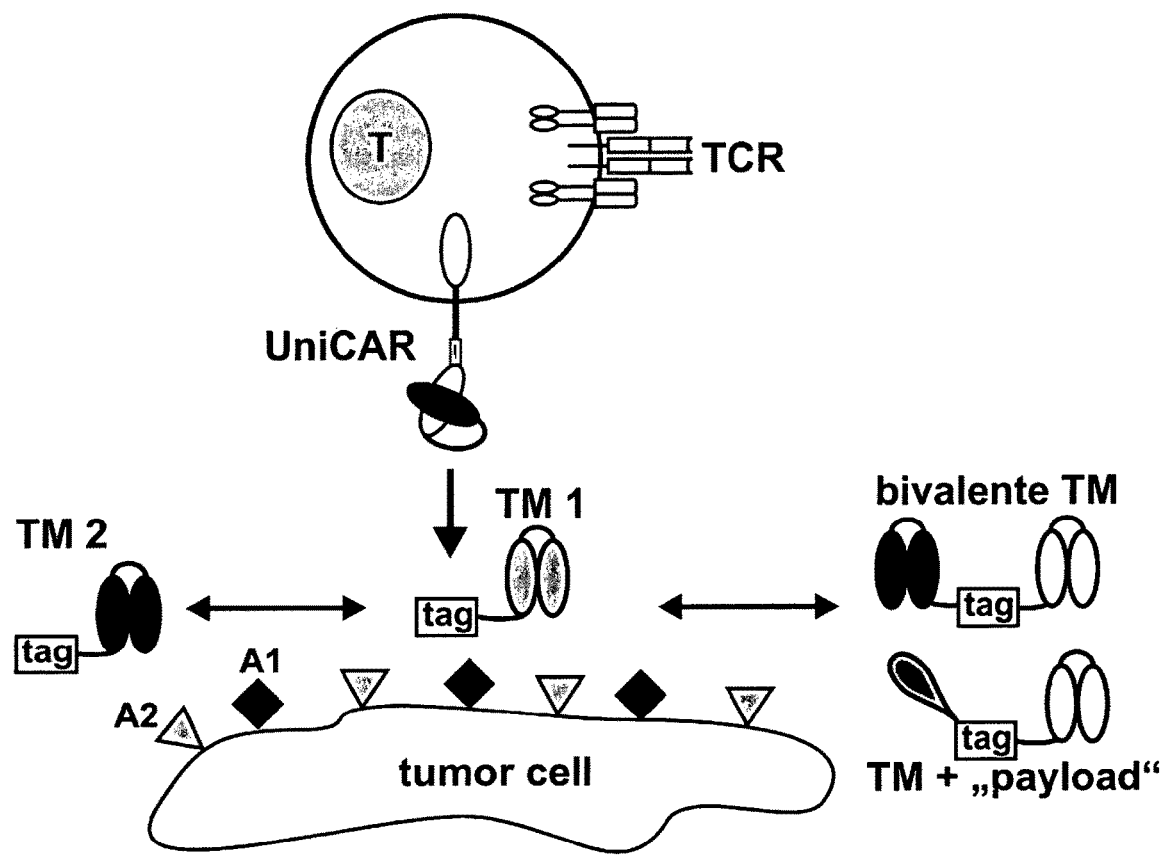

The UniCAR comprises three domains (FIG. 1). The first domain is the tag-binding domain. This domain is typically present at the amino terminal end of the polypeptide that comprises the UniCAR. Locating the tag-binding domain at the amino terminus permits the tag-binding domain unhampered access to the tagged target module that is bound to the target cell. The tag-binding domain is typically, but not restricted to, an antibody or an antigen-binding fragment thereof.

The identity of the antibody or fragment is only limited by the identity of the tag of the tagged target module. The tag can be derived from any human nuclear protein, against which an antibody or other binding domain is available. The antibody may be obtained from any species of animal, though preferably from a mammal such as human, simian, mouse, rat, rabbit, guinea pig, horse, cow, sheep, goat, pig, dog or cat. Preferably the antibodies are human or humanized antibodies. Nor is there a limitation on the particular class of antibody that may be used, including IgGI, IgG2, IgG3, IgG4, IgM, IgAI, IgA2, IgD and IgE antibodies. Antibody fragments include single-chain variable fragment (scFv), single chain antibodies, F(ab')2 fragments, Fab fragments, and fragments produced by a Fab expression library, with the only limitation being that the antibody fragments retain the ability to bind the selected tag. The antibodies may also be polyclonal, monoclonal, or chimeric antibodies, such as where an antigen binding region (e.g., F(ab')2 or hypervariable region) of a non-human antibody is transferred into the framework of a human antibody by recombinant DNA techniques to produce a substantially human molecule. Antigen-binding fragments, such as scFv, may be prepared therefrom. Antibodies to a selected tag may be produced by immunization of various hosts including, but not limited to, goats, rabbits, rats, mice, humans, through injection with a particular protein or any portion, fragment or oligopeptide that retains immunogenic properties of the protein.

Depending on the host species, various adjuvants can be used to increase the immunological response. Such adjuvants include, but are not limited to, detoxified heat labile toxin from *E. coli*, Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and *Corynebacterium parvum* are also potentially useful adjuvants. Antibodies and fragments thereof can be prepared using any technique that provides for the production of antibody molecules, such as by continuous cell lines in culture for monoclonal antibody production. Such techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci 80:2026-2030 (1983)), and the EBV-hybridoma technique (Cole et al., Monoclonal Antibodies and Cancer Therapy, Alan R. Liss Inc, New York N.Y., pp 77-96 (1985)). Techniques developed for the production of "chimeric antibodies", i.e., the splicing of mouse antibody genes to human antibody genes to obtain a molecule with appropriate antigen specificity and biological activity can also be used (Morrison et al., Proc Natl. Acad. Sci 81:6851-6855 (1984); Neuberger et al., Nature 312:604-608 (1984); Takeda et al., Nature 314:452-454 (1985)). Alternatively, techniques described for the production of single chain antibodies can be adapted to produce tag-specific single chain antibodies.

In one aspect, the tag-binding domain is a single-chain variable fragment (scFv). A scFv comprises the variable regions of the heavy (VH) and light chains (VL) of an antibody, typically linked via a short peptide of ten to about 25 amino acids. The linker can either connect the N-terminus of the V H with the C-terminus of the VL, or vice versa.

As indicated above, the binding specificity of the tag-binding domain will depend on the identity of the tag that is conjugated to the protein that is used to bind target structures.

Figure 3:
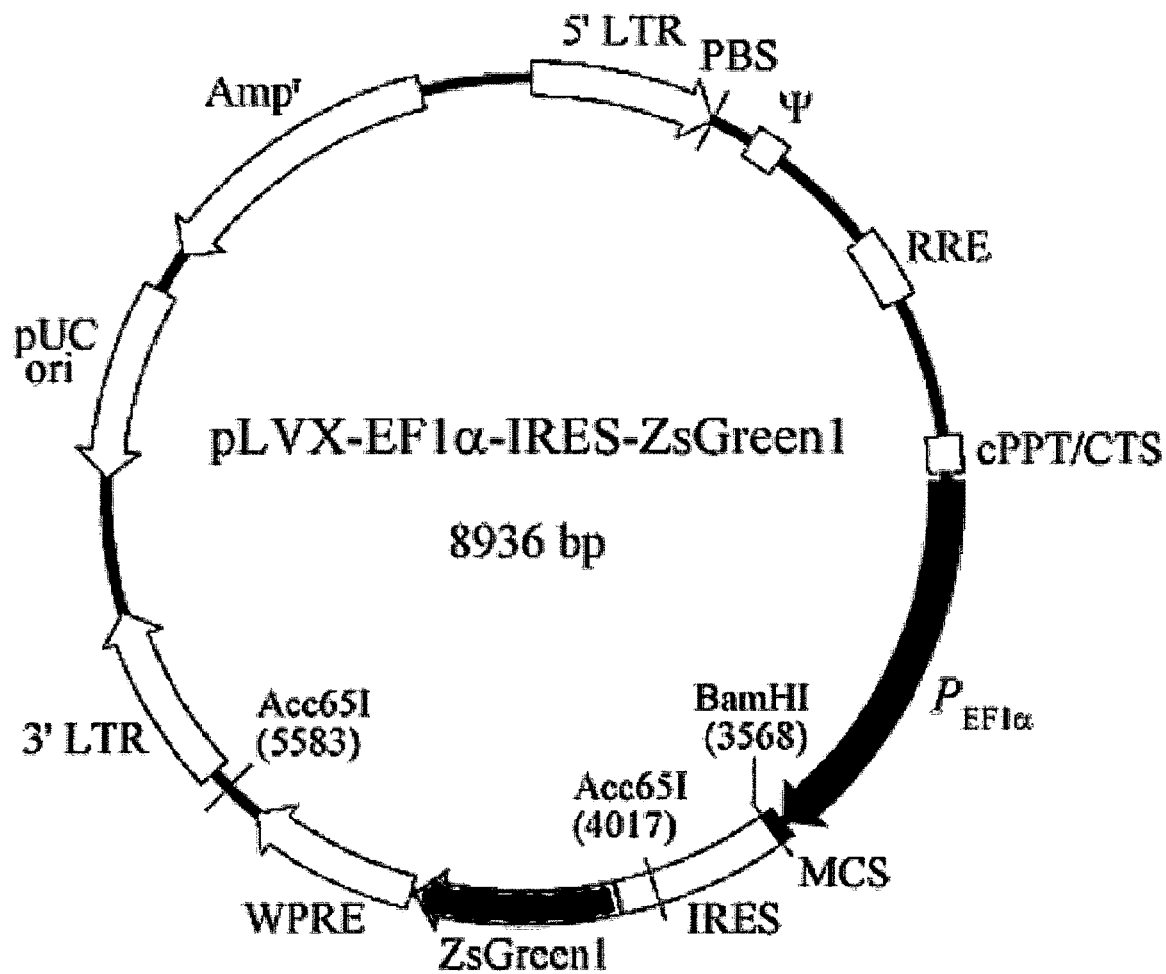

In a preferred embodiment the tag is a short linear epitope from the human nuclear La protein (E5B9), the tag-binding domain may constitute an antibody or an antibody-derived antigen-binding fragment, e.g. a single-chain fragment variable (scFv) binding to the respective La epitope (5B9). The use of the 5B9 anti-La epitope in the UniCAR system is advantageous due to the fact that the anti-La epitope scFv does not interact with native La protein bound to the surface of cells under normal physiological conditions. Thus, undesired interaction of UniCAR expressing immune cells, e.g. T or NK cells, with 5B9 epitope on native La is impossible. This leads to minimization of risk of uncontrolled on-target off-site toxicities by UniCAR expressing immune cells like release of toxic levels of cytokines, referred to variously as cytokine storms or cytokine release syndrome (CRS). Reactivity of the respective mab with denatured La protein in a western blot, but not with native La protein in an immunoprecipitation experiment was confirmed (FIG. 3). Moreover, while Sjogren's syndrome and systemic lupus erythematosus patients generate auto-antibodies against a variety of La epitopes, no auto-antibodies against E5B9 have been identified, which suggest that this epitope is not immunogenic (Yiannaki et al., Clin Exp Immunol., 112(1):152-8 (1998).

The second domain of the UniCAR is an extracellular hinge and a transmembrane (TM) domain. The hinge domain allows the UniCAR to protrude from the surface of the effector cell for optimal binding to its particular tag. The TM domain anchors the UniCAR into the cell membrane of the effector cell. Exemplary hinge and TM domains include, but are not limited to, the hinge and transmembrane regions of the human CD28 molecule, the CD8a chain, NK cell receptors like natural killer group 2D (NKG2D), or parts of the constant region of an antibody as well as combinations of various hinge and TM domains.

The third domain, when present, is the signal transduction domain. This domain transmits a cellular signal into the UniCAR carrying effector cell upon cross-linkage of the effector cell to a cell or extracellular structure. Cross-linkage between effector and target cell is mediated and depends on the presence of (i) a target module which binds to its particular binding moiety on the target cell or target extracellular structure and carries a tag and (ii) the UniCAR expressed on the surface of the effector cell can recognize and bind to the lag included in the target module. Effector cell activation includes induction of cytokines or chemokines as well as activation of cytolytic, phagocytic or suppressive activity of the effector cell. Exemplary effector cell signal transduction domains include, but are not limited to, the cytoplasmic regions of CD28, CD137 (41 BB), CD134 (OX40), DAP 10 and CD27, which serve to enhance T cell survival and proliferation; inhibitory receptors as programmed cell death-1 (PD-1) and cytotoxic T-lymphocyte antigen 4 (CTLA-4) as well as cytoplasmic regions of the CD3 chains (e.g. CD3zeta), DAP12 and Fc receptors, which induce T and NK cell activation. One or more than one signal transduction domain may be included in the UniCAR, such as two, three, four or more immune cell activating or costimulatory domains.

In a further embodiment the UniCAR comprises a fourth domain which is a short peptide linker in the extracellular portion of the UniCAR (FIG. 1). It is required for its functionality, that this fourth domain forms a linear epitope which allows the binding of a specific monoclonal antibody with reasonable affinity. One or more than one linear epitope may be included in the fourth domain and they may be located as linker in the tag-binding domain, in between the tag-binding domain and the extracellular linker or an integral part of the extracellular hinge domain. With the help of the optional fourth domain UniCAR engrafted immune cells can be specifically stimulated, so that UniCAR engrafted immune cells proliferate preferentially and persist longer compared to non-engrafted immune cells either in vitro or in vivo. The fourth domain may be also used to purify UniCAR engrafted immune cells from mixed cell populations. It may be also used to dampen UniCAR engrafted immune cell mediated immune response and to eliminate UniCAR engrafted immune cells in vivo.

For allow for expression on the cell surface of an effector cell, a signal peptide (sometimes also referred to as signal sequence, targeting signal, or leader peptide) is put in front of the tag-binding domain at the N-terminus of the UniCAR nuclide acid sequence. Signal peptides target proteins to the secretory pathway either co-translationally or post-translationally. For this purpose signal peptides from proteins of various species can be utilized, however preferentially leader peptides from proteins like CD28, CD8alpha, IL-2 or the heavy or light chain of antibodies of human origin are used to avoid immunogenic reactions.

Target Modules

Target modules are composed of a binding moiety specific for a certain human cell surface protein or protein complex and a tag. Target modules are administered to a subject prior to, or concurrent with, or after administration of the UniCAR-expressing effector cells. Alternatively, UniCAR expressing effector cells may be decorated with target modules prior to the infusion into the recipient. The binding moiety of target modules include, but are not limited to, antibodies or fragments thereof that bind to surface antigens like CD2, CD3, CD4, CD8, CD10, CD19, CD20, CD22, CD23, CD33, CD38, CD44, CD52, CD99, CD123, CD274 and TIM-3, members of the epidermal growth factor receptor family (erbI, erb2, erb3, erb4 and mutants thereof), members of the ephrin receptor family (EphA1-10, EphB1-6), so called prostate specific antigens (e.g. prostate stem cell antigen PSCA, prostate specific membrane antigen PSMA), embryonic antigens (e.g. carcinoembryonic antigen CEA, fetal acetylcholine receptor), members of the vascular endothelia growth factor family (VEGFR 1-3), epithelia cell adhesion molecule EpCAM, alphafetoprotein AFP, members of the mucin protein family (e.g. MUC1, MUC16), follicle stimulating hormone receptor (FSHR), the human high molecular weight-melanoma-associated antigen (HMW-MAA), folate binding protein FBP, a-Folate receptor, ligands of the NKG2D receptor, members of the epithelia glycoprotein family (e.g. EGP-2, EGP-4), diasialogangliosides (e.g. GD2, GD3), members of the carbonic anhydrase family (e.g. CAIX), and members of the carbohydrate antigen family (e.g. Ley), including mutants of the named proteins and protein families. In addition, the binding moiety of target modules include, but are not limited to, antibodies or fragments thereof that binds to cytoplasmic or nuclear antigens like the La/SSB antigen, members of the Rho family of GTPases, members of the high mobility group proteins and others. Likewise, the binding moiety of a target module can be composed of the alpha and beta or the gamma and delta chains of a T cell receptor (TCR) or fragments thereof. Such TCR-derived binding moieties recognize and bind to peptides presented by human leukocyte antigen class (HLA) I and II protein complexes. Examples are, but are not limited to, TCRs specific for peptides derived from proteins like EGFR family, survivin, sry-like high motility group box (SOX) protein family, melanoma-associated antigens (e.g. autoimmunogenic cancer/testis antigen NY-ESO-1, members of the melanoma antigen family A MAGEA, the preferentially expressed antigen in melanoma FRAME), and leukemia-associated antigens (e.g. wilms tumor gene 1 WT1). The binding moiety of target modules can also comprise ligands to proteins and protein complexes, further on referred as receptors. Such ligands may bind to, but are not limited to, cytokine receptors (e.g. IL-13 receptor), ligands of the NKG2D receptor, ligands to the EGFR family members, or auto-reactive TCRs.

Binding moieties of target modules may comprise single antigen specificity (monospecific), two, three or more antigen specificities (bi- and multispecific). Examples for bi- and multispecific antigen specificities include, but are not limited to, target modules binding to PSCA and PSMA antigen, CD19 and CD20 antigen, CD19, CD20, and CD22 antigen, CD33 and CD123 antigen, CD33 and CD99, CD33 and TIM-3, erb-1 and -2, PSCA and erb-2 and further combinations.

Binding moieties of target modules may also comprise monovalent binding as well a bi- and multivalent binding sites. Examples for bi- and multivalent targeting strategies include, but are not limited to, target modules incorporating two scFvs recognizing different epitopes of PSCA, CD19 and CD33, and ligand-scFv combinations recognizing different epitopes of the erbI receptor.

Target modules may also carry additional ligands, which are not involved in the target antigen binding, further on referred to as payloads. Such payloads may comprise, but are not limited to, costimulatory ligands or cytokines fused to the N- or C-terminus of the target module, in particular the extracellular domain of CD28, CD137 (41 BB), CD134 (OX40), and CD27, as well as IL-2, IL-7, IL-12, IL-15, IL-17, and 11-21, which all stimulate different kinds of immune cells. Other payloads may be radionuclides or chemical compounds which induce cell death in the target and neighboring cells.

Method

A method for stimulating a universal chimeric antigen receptor-mediated immune response in a mammal, the method comprising:

administering to a mammal an effective amount of an effector cell genetically modified to express a universal chimeric antigen receptor, wherein the universal chimeric antigen receptor comprises three domains, wherein the first domain is a tag-binding domain, the second domain is an extracellular hinge and a transmembrane domain and the third domain is a signal transduction domain, wherein tag-binding domain binds to a tag derived from any human nuclear protein and administering a target module composed of a binding moiety specific for a certain human cell surface protein or protein complex and a tag, wherein the tag is derived from any human nuclear protein, wherein the target modules are administered to a subject prior to, or concurrent with, or after administration of the universal chimeric antigen receptor-expressing effector cells.

In a preferred embodiment the effector cells and target module are administered to humans.

UniCAR Effector Cell Production.

In an embodiment of the invention, immune cells may be genetically engineered to express UniCARs by various methods. In general, a polynucleotide vector encoding the UniCAR and all necessary elements to ensure its expression in the genetically engineered immune cell is transferred into the cell. The transfer of the vector can be performed, but is not limited to, by electroporation or transfection of nucleid acids or the help of viral vector systems like, but not limited to, adeno-, adeno-associated, retro-, foamy- or lentiviral viral gene transfer.

In a further embodiment, lentiviral gene transfer may be applied for stable expression of UniCARs in immune cells by first constructing a lentiviral vector encoding for a selected UniCAR. An exemplary lentiviral vector includes, but is not limited to, the vector pLVX-EF1 alpha UniCAR 28/t (Clontech, Takara Bio Group) as shown in FIG. 3, in which the lentiviral parts of the vector are derived from the human immunodeficiency virus (HIV).

For the described application, the MSC/IRES/ZxGreenI portion was replaced by the UniCAR construct. Regarding FIG. 3 abbreviation used as following:

5' LTR: 5' long terminal repeat, PBS: primer binding site, LP: packaging signal, RRE: Rev-response element, cPPT/CTS: (central polypurine tract/central termination sequence, PEF1a: human elongation factor 1 alpha promoter, MCS: multiple cloning site, IRES: internal ribosome entry site, ZsGreenI: human-codon-optimized, WPRE: woodchuck hepatitis virus posttranscriptional regulatory element, 3' LTR: 3' long terminal repeat, pUC: origin of replication, Ampr: ampicillin resistance gene; β-lactamase.

Figure 4:
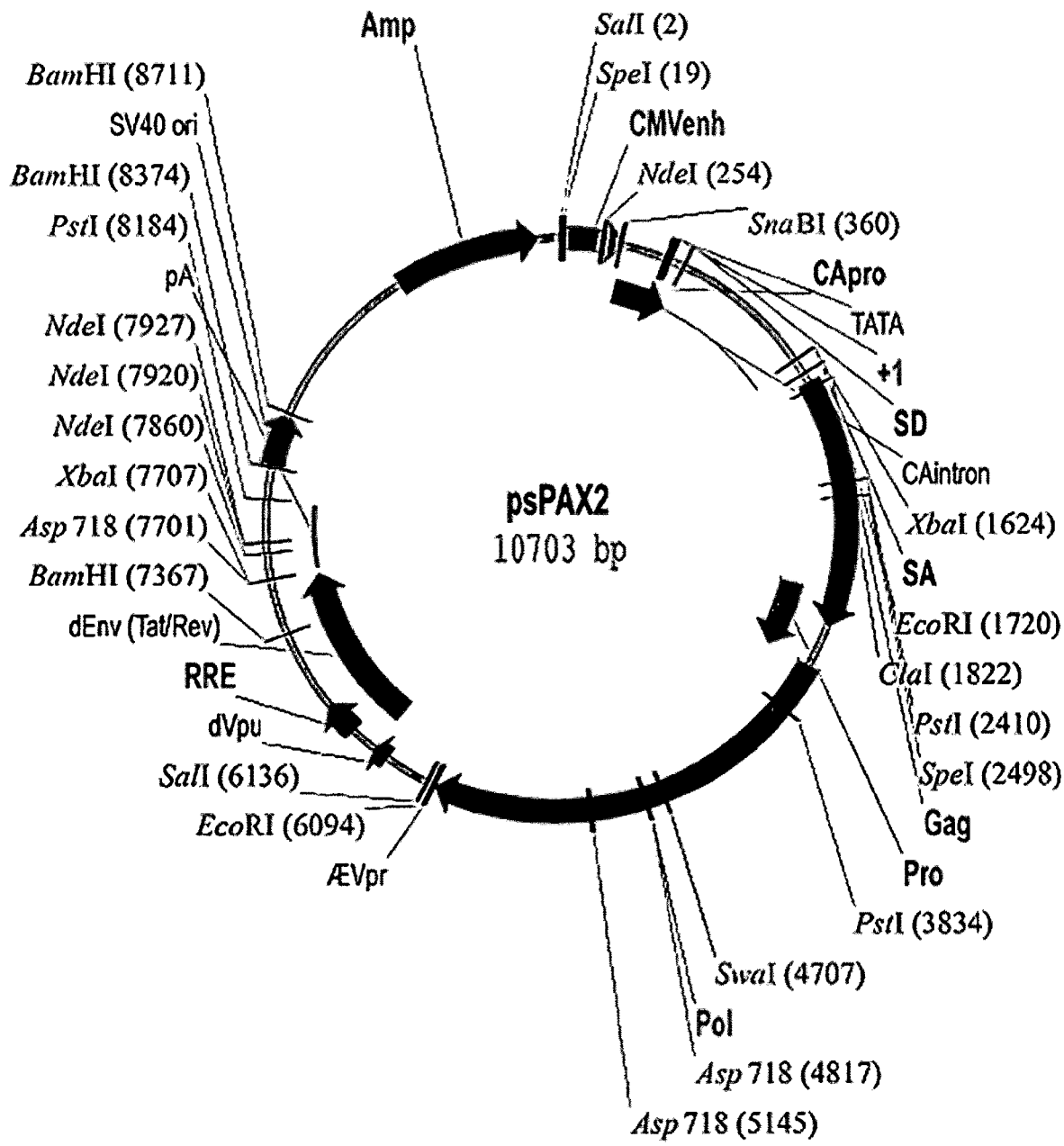
Figure 5:
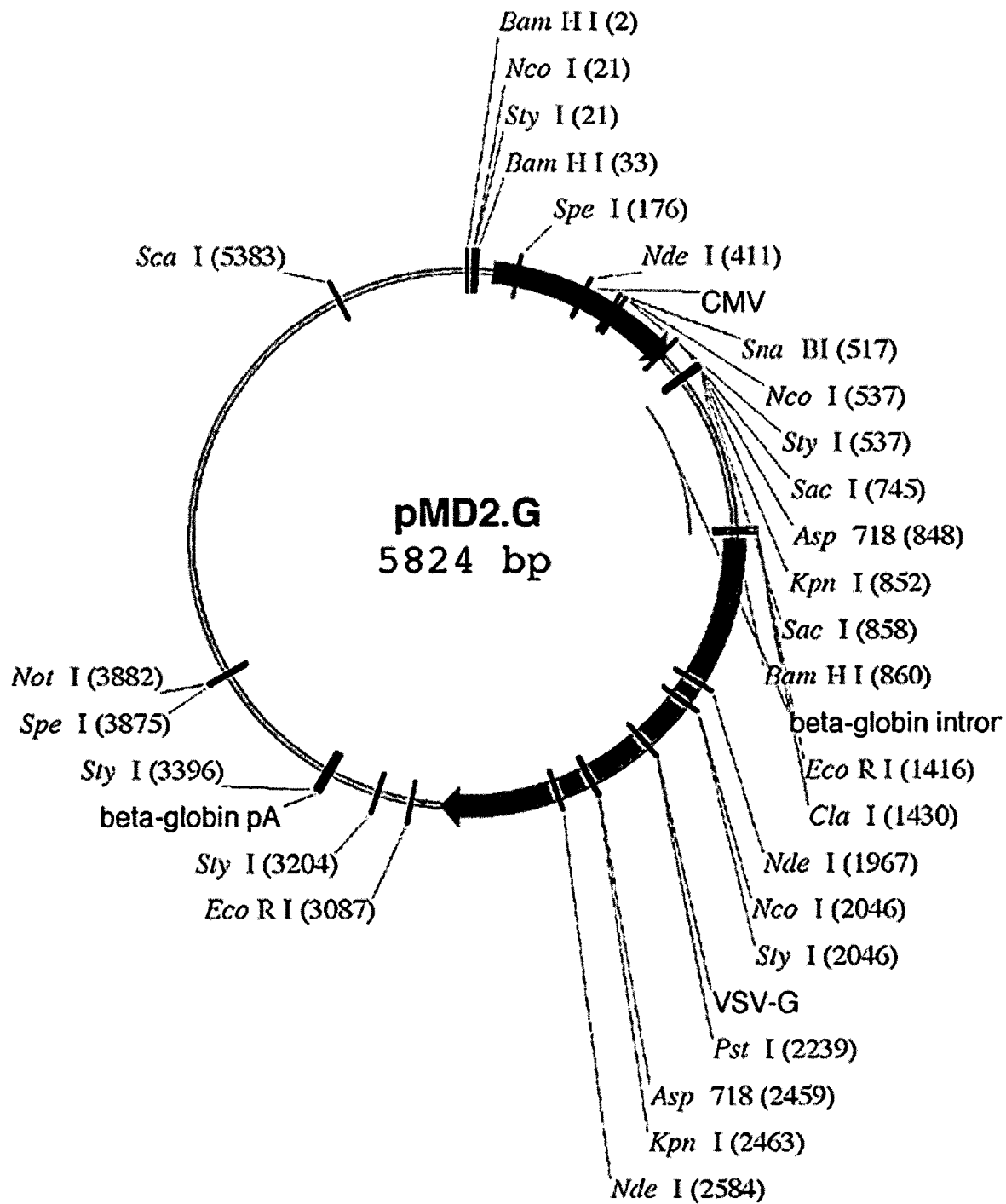

Lentiviral particles are typically produced by transient transfection of Human Embryonal Kidney (HEK) 293T (ACC 635) cells with the UniCAR encoding lentiviral vector plasmid and cotransfection with a group specific antigen (gag) and Polymerase (pol) encoding plasmid (e.g. psPAX2, addgene plasmid 12260) as depicted in FIG. 4 plus a plasmid encoding for an envelope (e.g. pMD2.G, addgene plasmid 12259) as shown in FIG. 5. After transfection the packaging plasmid expresses Gag and Pol protein of HIV-1. Abbrevation used in FIG. 4 as following: CMVenh: CMV enhancer and promoter, SD: splice donor, SA: splice acceptor, Gag: Group-specific antigen, Pro: Precursor protein encoding the protease protein, Pol: Protein encoding the reverse transcriptase and integrase, RRE: rev responsive element, Amp: ampicillin.

The plasmid MD2.G (FIG. 5) encodes the glycoprotein of the Vesicular Stomatitis Virus (VSV-G). VSV-G protein is used to lentiviral vectors to transduce a broad range of mammalian cells. Abbrevation used in FIG. 5 as following: CMV: CMV enhancer and promoter, beta-globin intror: beta-globin intron, beta-globin pA: beta-globin poly adenosine tail.

Various envelopes from different virus species can be utilized for this purpose. Lentiviral vectors can successfully pseudotype, but are not limited to, with the envelope glycoproteins (Env) of amphotropic murine leukemia virus (MLV) or the G protein of vesicular stomatitis virus (VSV-G), a modified envelope of the prototypic foamy virus (PFV) or chimeric envelope glycoprotein variants derived from gibbon ape leukemia virus (GaLV) and MLV. Supernatants from transfected HEK293T cells can be harvested 24 h to 96 h after transfection and virus particles may, but not necessarily have to, be concentrated from the supernatant by ultracentrifugation or other methods. For lentiviral transduction of immune cells various established protocols can be applied. In one aspect, peripheral blood mononuclear cells (PBMC) or isolated T cells can be activated with mab specific for the CD3 complex, e.g. clone OKT3 or UCHT1, either given in solution or coated to plastic cell culture dishes or magnetic beads Activation of PBMC or isolated T cells can be further enhanced by stimulating costimulatory pathways with mabs or ligands specific for, but not limited to, CD27, CD28, CD134 or CD137 either alone or in various combinations and the supply with exogenous recombinant cytokines like, but not limited to, interleukin (IL)-2, IL-7, IL-12, IL-15 and IL-21. Concentrated or non-concentrated virus particles are added to PBMC or T cell cultures 24 h to 96 h after initial administration of activating CD3 antibodies and/or recombinant cytokines as single or multiple doses. Stable transduction of T cells may be determined flow cytometry after staining with tag-containing target modules for surface expression of UniCARs or mabs directed against the fourth domain of UniCARs from day 3 onwards after final administration of virus supernatant. UniCAR transduced T cells can be propagated in vitro by culturing them under supply of recombinant cytokines and activating anti-CD3 mabs.

In case the UniCAR harbors the optional fourth domain, a peptide sequence forming a linear epitope for a mab, immune cells genetically modified to express UniCARs can be specifically propagated in vitro by coating a mab or antibody fragments thereof binding to the fourth UniCAR domain to the surface of culture dishes or to beads of any kind, which are added to the cell culture at a defined ratio of, but not limited to, 1 bead to 1-4 UniCAR engrafted effector cells. The binding of surface-coated mabs to the UniCAR peptide domain induces cross-linkage of cell-surface expressed UniCARs and formation of an immune synapse, which leads to the activation of signal pathways specifically triggered by the signal domain of the UniCAR. Depending on the signal pathways induced, this may leads to enhance proliferation and sustained resistance against activation-induced cell death of the UniCAR carrying immune cells and therefore enrichment of UniCAR genetically modified immune cells in a mixed population.

The optional fourth domain, a peptide sequence forming a linear epitope for a mab, can be further utilized to enrich and purify UniCAR expressing immune cells from mixed populations. Enrichment and purification can be performed with the help of a mab or antibody fragments thereof binding to the fourth UniCAR domain to either mark UniCAR expressing cells for cell sorting or to transiently link the UniCAR expressing immune cell to small particles, which can be utilized for cell isolation. In one aspect, UniCAR engrafted immune cells are incubated with the mab recognizing the fourth domain. Next, magnetic beads are added, which are conjugated with antibodies or fragment's thereof directed against the species- and isotype specific heavy and light chains of the mab binding to the optional fourth domain. Thus, UniCAR expressing immune cells and magnetic beads are linked and can be trapped and separated from other immune cells in a magnetic field.

Figure 6:
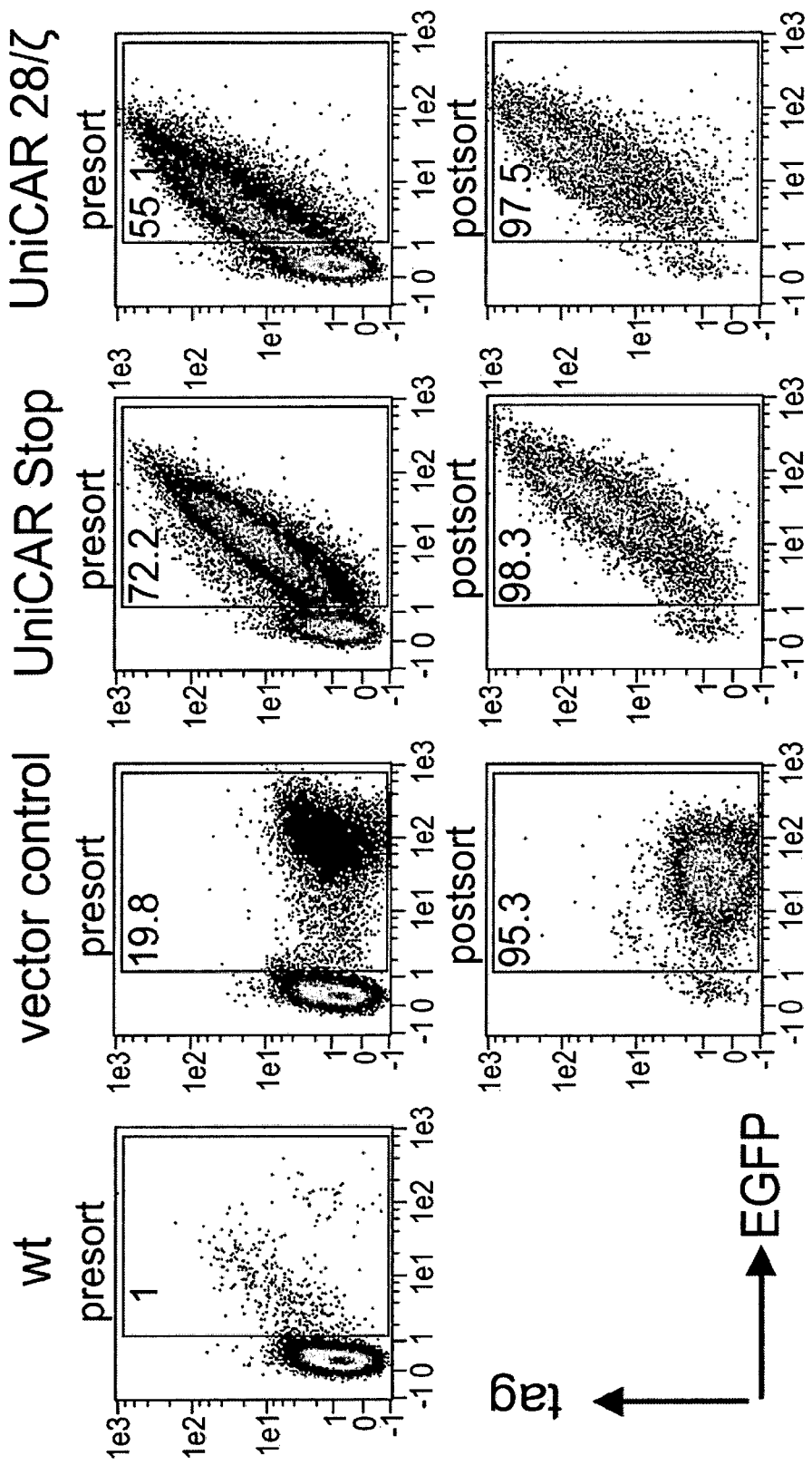

In a further embodiment of the invention the optional fourth domain can be used for detection of UniCAR surface expression as shown in FIG. 6. FIG. 6 (A) depicts that UniCAR surface expression can be detected by using a monoclonal antibody directed against the optional 4th domain and subsequently staining with a fluorochrome-conjugated anti-species secondary antibody. The optional 4th domain can be additionally used to purify UniCAR engrafted T cells to high purity as depicted in FIG. 6) in the UniCAR Immune Cell Administration.

Populations of UniCAR-expressing immune cells may be formulated for administration to a subject using techniques known to the skilled artisan.

Formulations comprising populations of UniCAR-expressing immune cells may include pharmaceutically acceptable excipient(s). Excipients included in the formulations will have different purposes depending, for example, on the nature of the tag-binding domain comprising the UniCARs, the population of immune cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubrbating agents. The formulations comprising populations of UniCAR-expressing immune cells will typically have been prepared and cultured in the absence of any non-human components, such as animal serum (e.g., bovine serum albumin).

A formulation may include one population or more than one, such as two, three, four, five, six or more populations of UniCAR-expressing immune cells. The different populations of UniCAR engrafted immune cells can vary based on the identity of the tag-binding domain, the identity of the signal transduction domain, the identity of the subpopulations, the mode of generation and cultivation or a combination thereof. For example, a formulation may comprise populations of UniCAR-expressing T and NK cells that recognize and bind to one, or more than one, such as two, three, four, five, six or more different tagged proteins.

The formulations comprising population(s) of UniCAR immune cells may be administered to a subject using modes and techniques known to the skilled artisan. Exemplary modes include, but are not limited to, intravenous injection. Other modes include, without limitation, intratumoral, intradermal, subcutaneous (s.c, s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of the formulations can be used to effect such administration. Injections can be performed as bulk injections or continuous flow injections.

The formulations comprising population(s) of UniCAR-expressing immune cells that are administered to a subject comprise a number of UniCAR-expressing immune cells that is effective for the treatment and/or prophylaxis of the specific indication or disease. Thus, therapeutically-effective populations of UniCAR-expressing immune cells are administered to subjects when the methods of the present invention are practiced. The number of UniCAR-expressing immune cells administered to a subject will vary between wide limits, depending upon the location, source, identity, extent and severity of the disease, the age and condition of the individual to be treated, etc. In general, formulations are administered that comprise between about $1\times10^4$ and about $1\times10^{10}$ UniCAR-expressing immune cells. In most cases, the formulation will comprise between about $1\times10^5$ and about $1\times10^9$ UniCAR-expressing immune cells, from about $5\times10^5$ to about $5\times10^8$ UniCAR-expressing immune cells, or from about $1\times10^6$ to about $1\times10^9$ UniCAR-expressing immune cells. A physician will ultimately determine appropriate dosages to be used. In case of adverse events, UniCAR engrafted immune cells can be depleted from an individual by the administration of a mab directed against the peptide domain (fourth domain) of the UniCAR forming a linear epitope for the respective antibody.

Target Module Production

Target modules comprise two domains, a binding moiety specific for a certain human cell surface protein or protein complex and a tag, against which the tag-binding domain of the UniCAR is directed. Target modules can be manufactured by techniques known to the skilled artisan. These techniques include, but are not limited to, recombinant expression in pro- or eukaryotic cells or artificial synthesis of polypeptide chains.

In one aspect, a target module may be expressed in Chinese ovarian hamster (CHO, ACC-110) cells, which are suitable for synthesizing high amount of recombinant proteins in their biologically active forms. A nucleic acid sequence coding for a target module can be transferred into CHO cells by established genetically engineering techniques like, but not limited to, naked nucleic acid transfection, electroporation or viral gene transfer. High productive single-cell clones may be selected from parental lines using, for example, the dihydrofolate reductase (DHFR) selection system. In this system, DHFR-deficient CHO cell mutants (e.g. CHO sub-line DXB11 or DG44) are genetically modified by co-transfection of a functional copy of the DHFR gene in addition to the nucleic acid sequence coding for a target module. Clonal selection is then performed by growth in media devoid of glycine, hypoxanthine and thymidine. High-productive clones can be further selected by culturing the cells in high levels of methotrexate (MTX), a folic acid analog that blocks DHFR activity. As gene modified cells must cope with the decrease in DHFR activity, which cannot be rescued by the mere presence of a single copy of the DHFR, clones with amplified copies of the DHFR gene are favored under these conditions. The genetic linkage between DHFR and the gene of interest ensures that the transgene is also co-amplified, thus enhancing chances of securing a high producing cell clone. Selected cell clones are grown under good manufacturing conditions preferential in the absence of any animal serum. Target modules may be isolated from cell culture supernatants by established preparative protein purification methods including preliminary steps like precipitation or ultracentrifugation and various purification techniques like, but not limited to, size exclusion or ion exchange chromatography. In one aspect, the nucleic acid sequence of a target module carries a coding sequence for six to eight successive histidine amino acids which form a polyhistidine tag. The polyhistidine binds strongly to divalent metal ions such as nickel and cobalt. Cell culture supernatant can be passed through a column containing immobilized nickel ions, which binds the polyhistidine tag, whereas all untagged proteins pass through the column. The target module can be eluted with imidazole, which competes with the polyhistidine tag for binding to the column, or by a decrease in pH, which decreases the affinity of the tag for the resin.

Target Module Administration

One target module or more than one, like two, three, four or more target modules may be formulated for administration to a subject using techniques known to the skilled artisan.

Formulations containing one or more than one target module(s) may include pharmaceutically acceptable excipient(s). Excipients included in the formulations will have different purposes depending, for example, on the nature of the target modules and the mode of administration.

Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The formulations comprising target modules will typically have been prepared and cultured in the absence of any non-human components, such as animal serum (e.g., bovine serum albumin).

A formulation may include one target module or more than one, such as two, three, four, five, six or more target modules. Target modules can vary based on the identity of the binding moiety, the identity of the tag, the mode of generation or a combination thereof. For example, a formulation may comprise target modules that recognize and bind to one, or more than one, such as two, three, four, five, six or more different human cell surface proteins, protein complexes or extracellular matrix structures.

Formulations comprising population(s) of UniCAR expressing immune cells may be incubated with a formulation including one or more target modules ex vivo, to decorate the UniCAR expressing immune cells with target modules before administration to a subject. Alternatively, formulations including one or more target modules can be administered directly to a subject or a combination of both strategies can be chosen. Route and dosage will vary between wide limits, depending upon the location, source, identity, extent and severity of the disease, the age and condition of the individual to be treated, etc. A physician will ultimately determine appropriate routes of application and dosages to be used.

Formulations comprising the target module are administered to a subject in an amount which is effective for treating and/or prophylaxis of the specific indication or disease. A typical dose-rate delivered per $m^2$ per day is between 1 μg to 1000 mg, preferably 10 pg to 1 mg, with dosages administered one or more times per day or week or continuously over a period of several weeks. However, the amount of target modules in formulations administered to a subject will vary between wide limits, depending upon the location, source, identity, extent and severity of the cancer, the age and condition of the individual to be treated, etc. A physician will ultimately determine appropriate dosages to be used.

The present invention relates to methods of treating a subject having cancer, infections or autoimmune disorders, comprising administering to a subject in need of treatment one or more formulations of target module, wherein the target module bind a cancer cell, and administering one or more therapeutically-effective populations of UniCAR expressing immune cells, wherein the UniCAR expressing immune cells bind the target module and induce cell death.

The term "cancer" is intended to be broadly interpreted and it encompasses all aspects of abnormal cell growth and/or cell division. Examples include: carcinoma, including but not limited to adenocarcinoma, squamous cell carcinoma, adenosquamous carcinoma, anaplastic carcinoma, large cell carcinoma, small cell carcinoma, and cancer of the skin, breast, prostate, bladder, vagina, cervix, uterus, liver, kidney, pancreas, spleen, lung, trachea, bronchi, colon, small intestine, stomach, esophagus, gall bladder; sarcoma, including but not limited to chondrosarcoma, Ewing's sarcoma, malignant hemangioendothelioma, malignant schwannoma, osteosarcoma, soft tissue sarcoma, and cancers of bone, cartilage, fat, muscle, vascular, and hematopoietic tissues; lymphoma and leukemia, including but not limited to mature B cell neoplasms, such as chronic lymphocytic leukemia/small lymphocytic lymphoma, B-cell prolymphocytic leukemia, lymphomas, and plasma cell neoplasms, mature T cell and natural killer (NK) cell neoplasms, such as T cell prolymphocytic leukemia, T cell large granular lymphocytic leukemia, aggressive NK cell leukemia, and adult T cell leukemia/lymphoma, Hodgkin lymphomas, and immunodeficiency-associated lymphoproliferative disorders; germ cell tumors, including but not limited to testicular and ovarian cancer; blastoma, including but not limited to hepatoblastoma, medulloblastoma, nephroblastoma, neuroblastoma, pancreatoblastoma, leuropulmonary blastoma and retinoblastoma. The term also encompasses benign tumors.

As used herein, the terms "treat", "treating", and "treatment" have their ordinary and customary meanings, and include one or more of: blocking, ameliorating, or decreasing in severity and/or frequency a symptom of cancer in a subject, and/or inhibiting the growth, division, spread, or proliferation of cancer cells, or progression of cancer (e.g., emergence of new tumors) in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

Administration frequencies of both formulations comprising populations of UniCAR expressing immune cells and formulations of target modules will vary depending on factors that include the disease being treated, the elements comprising the UniCAR expressing immune cells and the target modules, and the modes of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The duration of treatment will be based on the disease being treated and will be best determined by the attending physician. However, continuation of treatment is contemplated to last for a number of days, weeks, or months.

The present invention offers flexibility in the methods of treatment, and as a result, the formulation(s) of target modules and the population(s) of UniCAR expressing immune cells may be administered to a subject in any order. Thus, the formulation(s) of target modules may be administered to a subject before, after or concurrently with the population(s) of UniCAR expressing immune cells. Alternatively, where more than one formulation of target modules and/or more than one population of UniCAR expressing immune cells are administered to a subject, the administration can be staggered. For example, a first formulation of target modules can be administered, followed by a first population of UniCAR expressing immune cells, which is then followed by a second formulation of tagged proteins and then a second population of UniCAR expressing immune cells.

The present invention also includes methods whereby a population of UniCAR expressing immune cells is coated with target modules prior to administration of the UniCAR expressing immune cells to the subject.

In each of the embodiments of the present invention the subject receiving treatment is a human or non-human animal, e.g., a non-human primate, bird, horse, cow, goat, sheep, a companion animal, such as a dog, cat or rodent, or other mammal.

Figure 7:
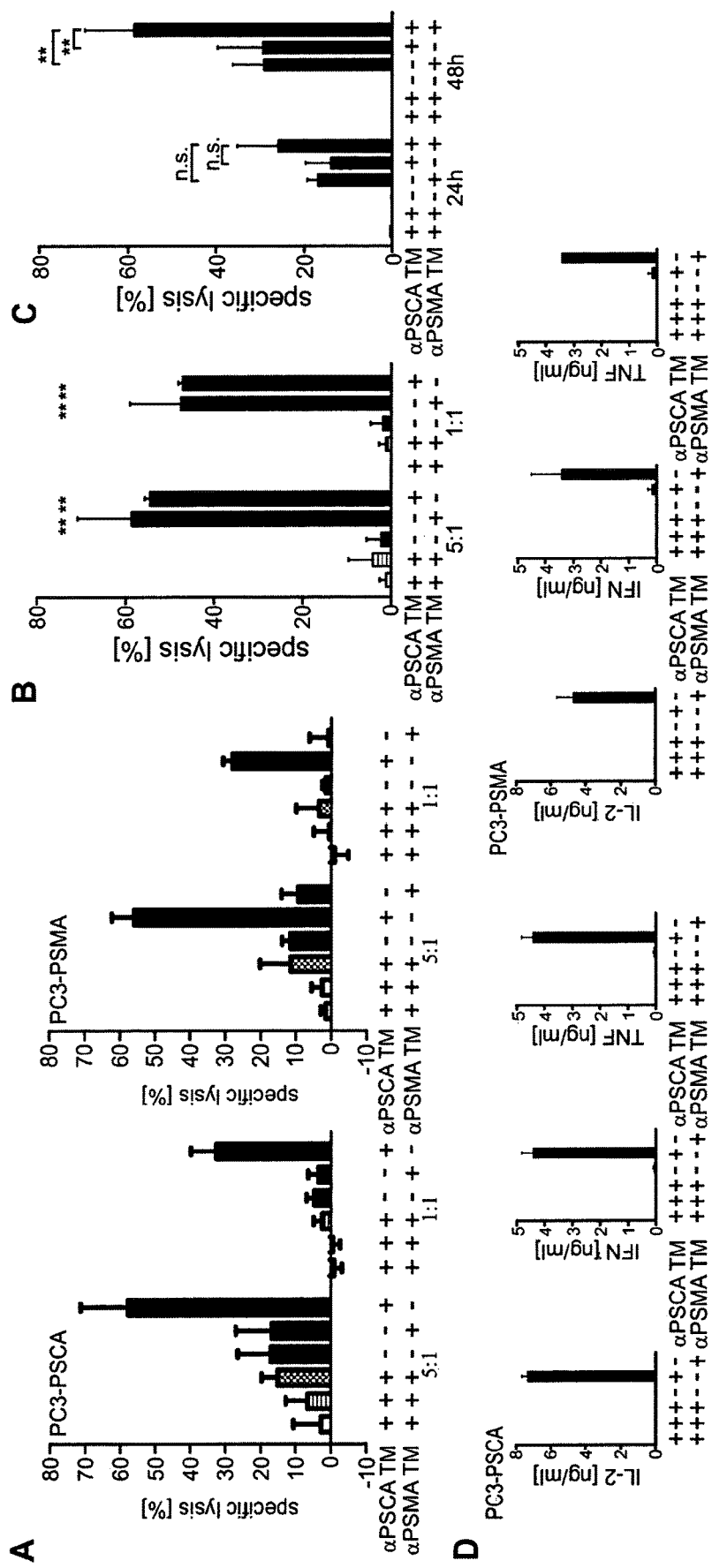

In an embodiment UniCAR genetically engineered T cells can be specifically redirected against tumor cells expressing PSCA and/or PSMA as frequently detected in biopsies e.g. from prostate, bladder, pancreatic and breast tumors (FIG. 7). Human T cells were mock transduced (white bars) or transduced with lentiviral vectors encoding the UniCAR containing a dual CD28/CD3zeta signaling domain (black bars) or lacking any signaling domain (hatched bars) or expressing only EGFP marker protein (stripped bars). Specific lysis of prostate tumor cells (PC3) genetically engineered to express either the prostate stem cell antigen (PC3-PSCA) or prostate membrane antigen (PC3-PSMA) in presence of engineered human T cells and target modules was analyzed in a 51Cr-release assay. T cells were incubated at an effector to target ratio (e:t) of 5:1 or 1:1 with 51Cr-loaded PC3 target cells. Target modules (TM) specific for PSCA (aPSCA TM) or PSMA (aPSMA TM) were added at a concentration of 15 nMol. After 20 h cultivation target cell lysis (chromium release) was measured. Plots show mean and s.d. from experiments with three individual T cell donors (FIG. 7A). Likewise the killing capacities of UniCAR engineered T cells against LNCap-4-2B tumor stem cells expressing both PSCA and PSMA antigen was demonstrated in the presence of either PSCA- or PSMA TM (1 nMol) by 51Cr release assays at the indicated e:t ratios. Mean and s.d. from experiments with three individual T cell donors is shown (FIG. 7B). The experiment from FIG. 7B was repeated at lower e:t ratio of 1:2 adding either 1 nMol PSCA- or PSMA specific TM or combining both TMs at a total concentration of 1 nMol. Specific lysis as determined by 51Cr release was measured after 24 h and 48 h. Mean and s.d. from experiments with three individual healthy T cell donors is shown (FIG. 7C). This experiment demonstrates, that the combination of two different TMs improves killing abilities of UniCAR redirected T cells against tumor cells in comparison to a single antigen retargeting strategy even if the total amount of both TMs in the double targeting sample equals total amount of each TM in the single antigen retargeting control sample (FIG. 7C). Moreover, human T cells armed with the UniCAR secret inflammatory and proliferative cytokines upon cross-linkage to antigen-expressing tumor cells in the presence of the corresponding TM (FIG. 7D). Human T cells were incubated with PC3 cells expressing either PSCA or PSMA antigen in presence or absence of TMs specifb for PSCA or PSMA. After 24 h cultivation cell-free supernatant was harvested and subsequently analyzed for the release of T cell specific cytokines using commercially available ELISA kits. Statistical analysis for FIG. 7C, D was performed using non-parametric one-way ANOVA (Kruskal-Wallis test) and post-hoc Dunn's Multiple Comparison test (**p<0.01).

Figure 8:
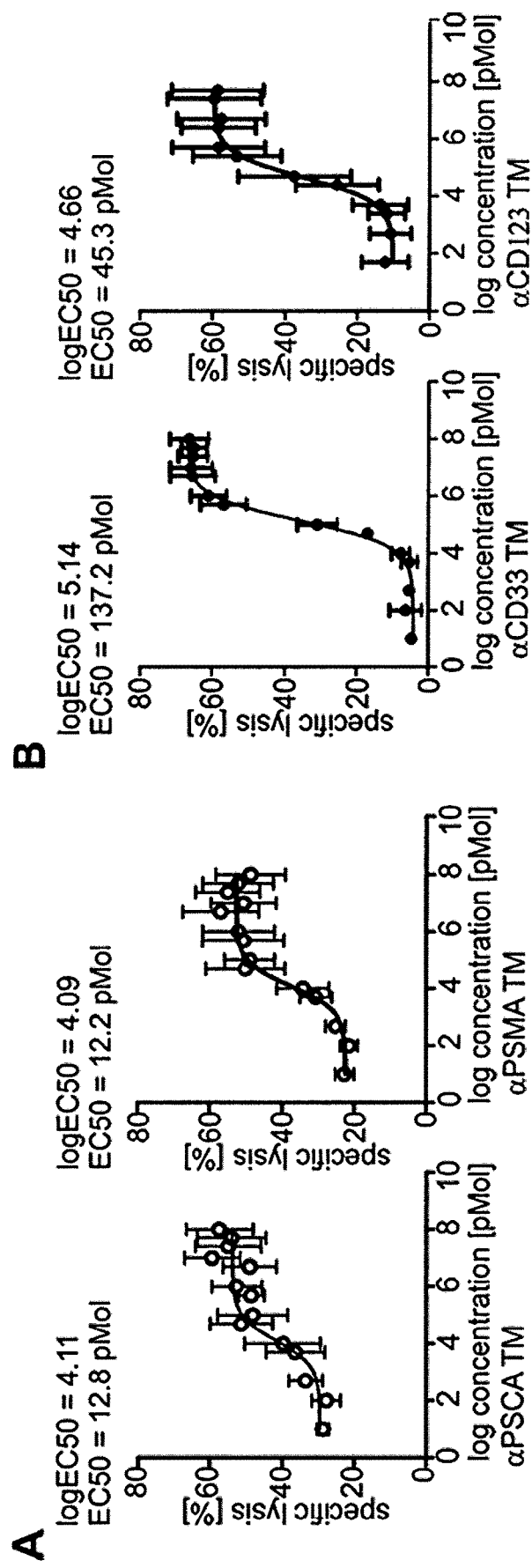
FIGS. 8A and 8B shows diagrams of concentration-response curves for different target moduls.

In a further embodiment FIG. 8 shows concentration-response curves for UniCAR genetically modified human T cells in the presence of target modules binding to various antigens on the surface of tumor cells of different origins. Human T cells were transduced with lentiviral vectors encoding the UniCAR containing a dual CD28/CD3zeta signaling domain. UniCAR engrafted T cells were incubated at an e:t ratio of 5:1 with 51Cr-loaded PC3 target cells genetically engineered to either express PSCA or PSMA antigen. Target modules (TMs) specific for PSCA (aPSCA TM) or PSMA (aPSMA TM) were added at increasing concentrations (FIG. 7A). Half maximal effective dosis (EC50) was determined to be approximately 12 pMol for both TMs. Additional experiments were performed as in FIG. 7A, but an e:t ratio of 1:1 was chosen and the acute myeloid leukemia cell line MOLM-13 was used as target tumor cells. TMs specific either for CD33 antigen (aCD33 TM) or CD123 antigen (aCD123 TM) were added at increasing concentrations and EC50 values of 137 pMol for aCD33 TM and 45 pMol for aCD123 TM were determined. These experiments demonstrates, that UniCAR engrafted T cells are effective at very low concentrations of TMs, which are 10 to 100 fold lower of EC50 values experimentally determined for monoclonal antibody drugs approved for cancer therapy (e.g. Herter et al. Mol Cancer Ther 12(10): 2031-2042 (2013)).

Figure 9:
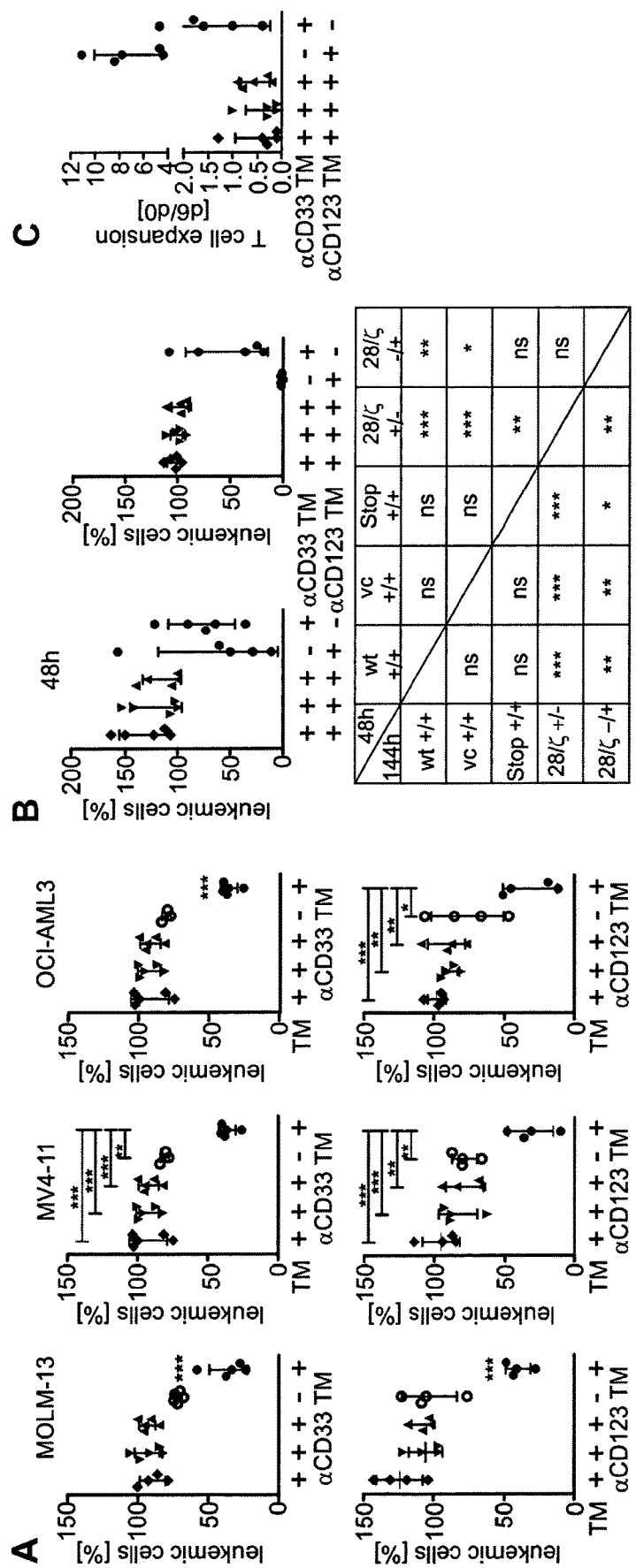
FIG. 9A-9C shows diagrams of effector functions of UniCAR engineered T cells against acute myeloid leukemia.

In a further embodiment FIG. 9 demonstrates that UniCAR engineered T cells can efficiently kill acute myeloid leukemia (AML) blasts. Human T cells were mock transduced (wt, rhombs) or transduced with lentiviral vectors encoding the U-CAR containing a dual CD28/CD3zeta signaling domain (CAR 28/$\zeta$, open and closed circles) or lacking any signaling domain (CAR Stop, up-pointing triangle) or expressing only EGFP marker protein (vc, down-pointing triangle). T cells were incubated with $2*10^4$ Alexa eFluor 674 labeled target cells from 3 AML cell lines (MOLM-13, MV4-11, OCI-AML3) in the presence (+) or absence (−) of 0.1 nMol CD33-specific (aCD33 TM, upper panel) or CD123-specific (aCD123 TM, lower panel) target moduls (TM) at an e:t ratio of 1:1 for 24 h (FIG. 9A). Number of living, propidiumiodid (PI) negative, but Alexa eFluor 674 positive target cells was determined by flow cytometry using a MACSQuant® Analyzer. The number of living leukemic target cells was normalized to a control sample with target cells but without any T cells. This experiment demonstrates that UniCAR engrafted T cells efficiently lyse AML blasts after cross-linkage with the corresponding TM independent of antigen density, which for CD33 is high on MOLM-13, intermediate on MV4-1 and low on OCI-AML3 whereas for CD123 antigen density is in the reverse order on the 3 cell lines. Moreover, AML blast are eliminated by UniCAR engrafted T cells upon TM mediated cross-linkage even at low e:t ratios as typically found in patient samples (FIG. 9B). Experimental set-up was similar to FIG. 9A, but a low e:t ratio of 1:5 was chosen. Number of living, PI negative T cells and target cells was determined by flow cytometry using a MACSQuant® Analyzer at the indicated time points. The number of living leukemic target cells was normalized to a control sample with target cells but lacking any T cells (FIG. 9B). Upon activation via CAR mediated signaling, UniCAR engrafted T cells start to proliferate as shown in FIG. 9C. Experimental set-up was as described for FIG. 9B and T cell numbers were determined by flow cytometry using a MACSQuant® Analyzer. T cell expansion was calculated as the ratio of T cells present in samples after 144 h (d6) to the number seeded at start of the experiment (dO). Statistical analysis for FIGS. 8A and B was performed using non-parametric one-way ANOVA (Kruskal-Wallis test) and post-hoc Dunn's Multiple Comparison test. For FIG. 9A significant statistic results are indicated, for FIG. 9B results are given in the table below the figure (ns=non-significant, * p<0.05, p<0.01, *p<0.001).

Figure 10:
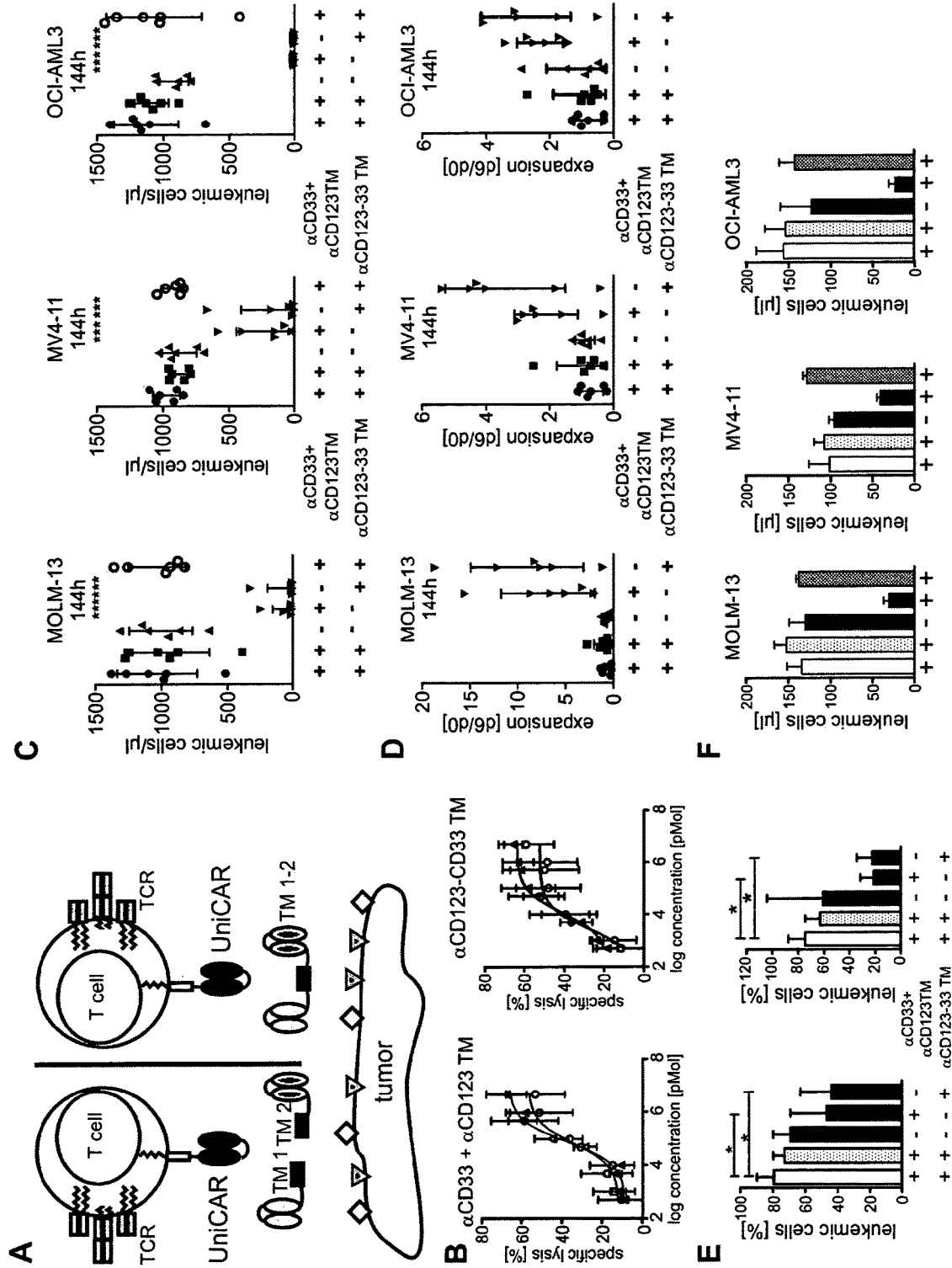
FIG. 10A-10F depicts diagrams showing redirection of T cells engrafted with UniCARs against two antigens simultaneously.
Figure 11:
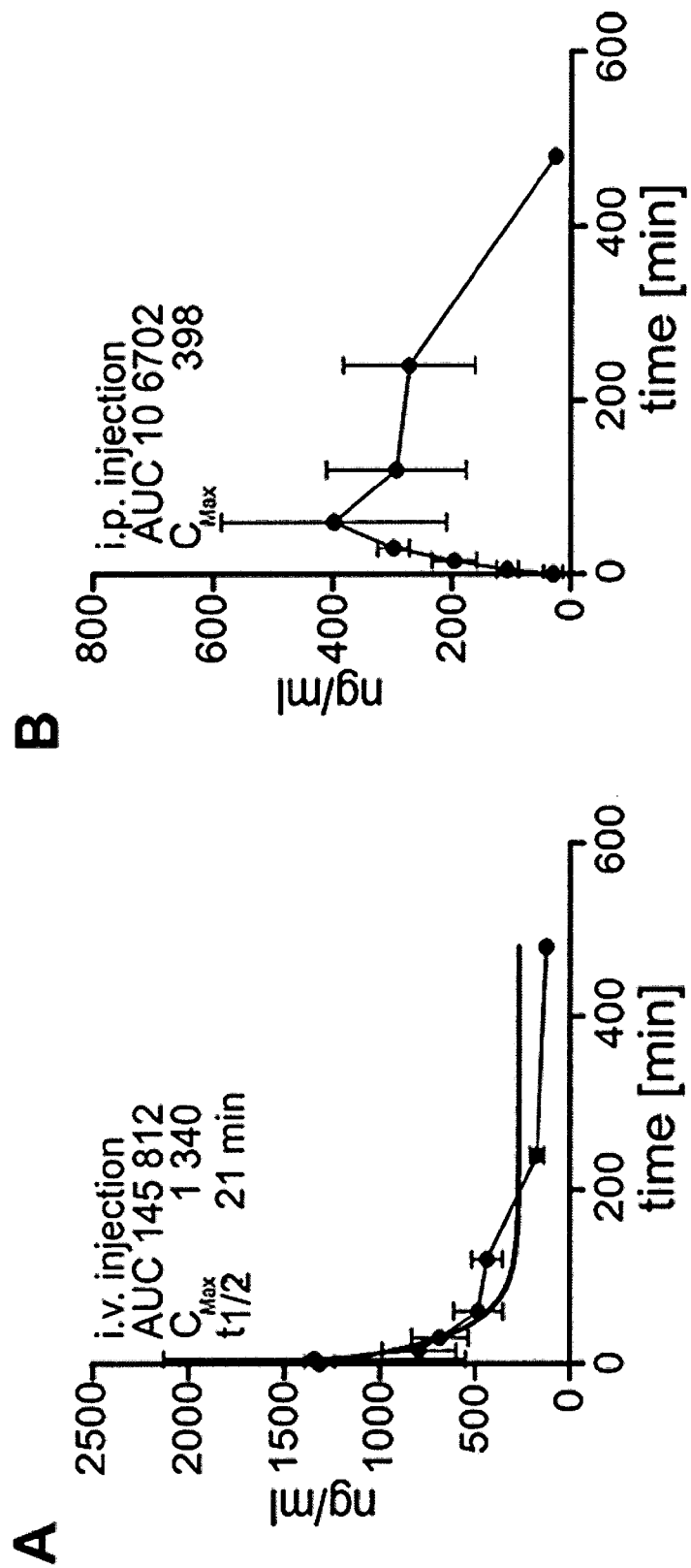
FIG. 11A-11B depicts diagrams showing in vivo pharmokinetics of bispecific αCD123-CD33 target module.

In a further embodiment FIG. 10 shows redirection of T cells engrafted with UniCARs against two antigens simultaneously. Due to its modular nature, the UniCAR technology allows a redirection of UniCAR engrafted immune cells (e.g. T cells) against two antigens simultaneously or consecutively using either two individual TMs (TM 1+TM 2, FIG. 10A left side), or combined bi-specific TMs (TM1-2, FIG. 10A right side) arranged as bispecific single chain tandem constructs (FIG. 10A). Using a bispecific TM targeting two antigens can be even more efficient than using a combination of two single-antigen specific TMs, as demonstrated by concentration-response curves for combined CD33- and CD123-specific retargeting of UniCAR engrafted T cells against AML cell lines (FIG. 10B). Human T cells were transduced with a lentiviral vector encoding the UniCAR containing a dual CD28/CD3zeta signaling domain. UniCAR engrafted T cells were incubated at an e:t ratio of 1:1 with Cr51-labeled MOLM-13 (mean from experiments with T cells from 4 different healthy human donors, triangles) and OCI-AML3 (mean from experiments with T cells from 2 different healthy human donors, open circles) for 24 h. Target modules (TM) specific for CD33 (aCD33 TM), CD123 (aCD123 TM) or bi-specific CD33-CD123 TM (aCD123-CD33 TM) were added at increasing concentrations. EC50 values were determined to be: aCD33+aCD123 TM: EC50 MOLM-13=70.2 pMol, EC50 OCI-AML3=80.2 pMol. aCD33-aCD123 TM: EC50 MOLM-13=2.9 pMol, EC50 OCI-AML3=11.7 pMol. Next it could be demonstrated, that UniCAR engrafted T cells from both healthy human donors and AML patients can be successfully redirected against AML cell lines as well as AML blasts isolated from patients in blast crisis (FIG. 100, D, E, F). Human T cells were mock transduced (closed circles in FIG. 10C, D, open bars in FIG. 10E, F) or transduced with lentiviral vectors encoding the UniCAR containing a dual CD28/CD3zeta signaling domain (triangles in FIG. 10C, D, black bars in FIG. 10E, F) or lacking any signaling domain (rhombs in FIG. 10C, D, grey bars in E, F). Highly efficient elimination of AML cells is mediated by UniCAR engrafted T cells in presence of either the combination of aCD33 TM and aCD123 TM or the dual targeting aCD123-CD33 TM, but not in the absence of the TMs, demonstrating again that for antigen specific redirection of UniCAR engrafted T cells the cross linkage via a TM is indispensable (FIG. 100, D, E). T cells were incubated with $2*10^4$ Alexa eFluor 674 labeled target cells from 3 AML cell lines (MOLM-13, MV4-11, OCI-AML3) in the presence (+) or absence (−) of total amount of 100 pMol TMs at an e:t ratio of 1:5 for 144 h. TMs were refreshed after 48 h. Number of living, PI negative but Alexa eFluor 674 positive target cells was determined by flow cytometry using a MACSQuant® Analyzer and compared to control samples with target cells but without any T cells (FIG. 100, open circles). T cell expansion was calculated as the ratio of T cells present in samples after 144 h (d6) to the number seeded at start of the experiment (d0) in FIG. 10D. Results from experiments with 6 donors are shown, mean and s.d. are indicated. These results convincingly demonstrate, that activation via UniCAR signaling upon TM mediated cross linkage not only leads to target cell killing, but in addition UniCAR engrafted T cells receive an proliferative stimulus by the combined CD28/CD3 UniCAR signaling chain and start to divide. Next, genetically modified T cells from healthy donors were incubated with $5*10^4$ Alexa eFluor 674 labeled leukemic cells from AML patients in the presence (+) or absence (−) of 0.5 nMol TMs at an e:t ratio of 1:1 (FIG. 10E). Number of living, Alexa eFluor 674 positive target cells was determined by flow cytometry using a MACSQuant® Analyzer after 24 h (left panel) and 48 h (right panel). The number of living leukemic target cells was normalized to a control sample with target cells but without any T cells. Results from 5 pairing experiments in FIG. 9E demonstrate, that UniCAR engineered T cells are capable to lyse AML blast from patients over time. It could be also demonstrated, that UniCAR genetically modified T cells from an AML patient are enabled to attack and lyse AML cells by adding AML antigen-specific TMs. Modified T cells were incubated with $2*10^4$ Alexa eFluor 674 labeled target cells from 3 AML cell lines (MOLM-13, MV4-11, OCI-AML3) for 24 h in the presence (+) or absence (−) of total amount of 0.5 nMol TM at an e:t ratio of 1:1. Number of living, PI negative but Alexa eFluor 674 positive target cells was determined by flow cytometry using a MACSQuant® Analyzer In a further embodiment FIG. 11 depicts diagrams showing in vivo pharmokinetics of bispecific aCD123-CD33 target module. NSG mice (NOD/SCI D IL2Ry−/−) were injected with 250 μg/g body weight aCD123-CD33 TM either intravenously (i.v. in FIG. 11A) or intraperitoneal (i.p. in FIG. 11B) and serum samples were taken at indicated time points. A capture ELISA was used to determine the concentration of TM in the samples. Result show mean and standard deviation (n=3). Half-time decay was determined for the i.v. injection using an exponential one phase decay model (software GraphPad Prism).

In a further embodiment an isolated nucleic acid sequence encoding a universal chimeric antigen receptor according to SEQ. ID 1 is provided. The isolated nucleic acid sequence encoding an human IL-2m leader peptide according to SEQ. ID 2, an humanized anti-La 5B9 variable region heavy chain according to SEQ. ID 3, an humanized anti-La 5B9 variable region light chain according to SEQ. ID 4, a La 7B6 epitope according to SEQ. ID 5, a human CD 28 according to SEQ. ID 6 to 8, including a human CD28 extracellular part with mutated binding motif according to SEQ. ID 6, a CD28 transmembrane domain according to SEQ. ID 7, and a human CD28 intracellular part including a mutated internalization motif according to SEQ. ID 8 and a human CD 3 zeta intracellular domain according to SEQ. ID 9.

The product of the protein expression of the isolated nucleic acid sequence according to SEQ. ID 1 can be obtained in SEQ. ID 27. The nucleic acid sequence of humanized anti-La 5B9 variable region heavy chain according to SEQ. ID 3 encodes for a protein according to SEQ. ID 33, whereas the humanized anti-La 5B9 variable region light chain according to SEQ. ID 4 encodes for a protein according to SEQ. ID 34.

The nucleic acid sequence of human La 7B6 epitope according to SEQ. ID 5 encodes for a protein domain according to SEQ. ID 35.

In a further embodiment of the invention an isolated nucleic acid sequence encoding a target module with a binding moiety for prostate specific antigens PSCA is provided in SEQ. ID 10. The isolated nucleic acid sequence encoding a leader peptid IgGkappa according to SEQ. ID 11, a humanized light chain of an anti-PSCA scFv according to SEQ. ID 12, a humanized heavy chain of an anti-PSCA scFv according to SEQ. ID 13, a La 5B9 epitop according to SEQ. ID 14, a myc tag according to SEQ. ID 15 and a his tag according to SEQ. ID 16.

The product of protein expression of the nucleic acid according to SEQ. ID 10 can be obtained from SEQ. ID 28. The nucleic acid sequence of the humanized light chain of an anti-PSCA scFv according to SEQ. ID 12 encodes for a protein domain according to SEQ. ID 36, whereas the humanized heavy chain of an anti-PSCA scFv according to SEQ. ID 13 encodes for a protein domain according to SEQ. ID 37. The La 5B9 epitop according to SEQ. ID 14 encodes for a protein according to SEQ. ID 44.

In a further embodiment of the invention an isolated nucleic acid sequence encoding a target module with a binding moiety for prostate specific antigens PSMA is provided in SEQ. ID 17. The isolated nucleic acid sequence encoding a leader peptid IgGkappa according to SEQ. ID 11, a humanized heavy chain of an anti-PSMA scFv according to SEQ. ID 18, a humanized light chain of an anti-PSMA scFv according to SEQ. ID 19, a La 5B9 epitop according to SEQ. ID 14, a myc tag according to SEQ. ID 15 and a his tag according to SEQ. ID 16.

The product of protein expression of the nucleic acid according to SEQ. ID 17 can be obtained from SEQ. ID 29. The nucleic acid sequence of the humanized heavy chain of an anti-PSMA scFv according to SEQ. ID 18 encodes for a protein domain according to SEQ. ID 38, whereas the humanized light chain of an anti-PSMA scFv according to SEQ. ID 19 encodes for a protein domain according to SEQ. ID 39. The La 5B9 epitop according to SEQ. ID 14 encodes for a protein according to SEQ. ID 44.

In a further embodiment of the invention an isolated nucleic acid sequence encoding a target module with a binding moiety for anti-CD33 antigen is provided in SEQ. ID 20. The isolated nucleic acid sequence encoding a leader peptid IgGkappa according to SEQ. ID 11, a humanized light chain of an anti-CD33 scFv according to SEQ. ID 21, a humanized heavy chain of an anti-CD33 scFv according to SEQ. ID 22, a La 5B9 epitop according to SEQ. ID. 14, a myc tag according to SEQ. ID 15 and a his tag according to SEQ. ID 16.

The product of protein expression of the nucleic acid according to SEQ. ID 20 can be obtained from SEQ. ID 30. The nucleic acid sequence of the humanized light chain of an anti-CD33 scFv according to SEQ. ID 21 encodes for a protein domain according to SEQ. ID 40, whereas the humanized heavy chain of an anti-CD33 scFv according to SEQ. ID 22 encodes for a protein domain according to SEQ. ID 41. The La 5B9 epitop according to SEQ. ID 14 encodes for a protein according to SEQ. ID 44.

In a further embodiment of the invention an isolated nucleic acid sequence encoding a target module with a binding moiety for anti-CD123 antigen is provided in SEQ. ID 23. The isolated nucleic acid sequence encoding a leader peptid IgGkappa according to SEQ. ID 11, a humanized heavy chain of an anti-CD123 scFv according to SEQ. ID 24, a humanized light chain of an anti-CD123 scFv according to SEQ. ID 25, a La 5B9 epitop according to SEQ. ID 14, a myc tag according to SEQ. ID 15 and a his tag according to SEQ. ID 16.

The product of protein expression of the nucleic acid according to SEQ. ID 23 can be obtained from SEQ. ID 31. The nucleic acid sequence of the humanized heavy chain of an anti-CD123 scFv according to SEQ. ID 24 encodes for a protein domain according to SEQ. ID 42, whereas the humanized light chain of an anti-CD123 scFv according to SEQ. ID 25 encodes for a protein domain according to SEQ. ID 43. The La 5B9 epitop according to SEQ. ID 14 encodes for a protein according to SEQ. ID 44.

In a further embodiment of the invention an isolated nucleic acid sequence encoding a target module with a binding moiety for anti-CD123-anti-CD33 antigen is provided in SEQ. ID 26. The isolated nucleic acid sequence encoding a leader peptid IgGkappa according to SEQ. ID 11, a humanized heavy chain of an anti-CD123 scFv according to SEQ. ID 24, a humanized light chain of an anti-CD123 scFv according to SEQ. ID 25, a La 5B9 epitop according to SEQ. ID 14, a humanized heavy chain of an anti-CD33 scFv according to SEQ. ID 22, a humanized light chain of an anti-CD33 scFv according to SEQ. ID 21, a myc tag according to SEQ. ID 15 and a his tag according to SEQ. ID 16.

The product of protein expression of the nucleic acid according to SEQ. ID 26 can be obtained from SEQ. ID 32. The nucleic acid sequence of the humanized heavy chain of an anti-CD123 scFv according to SEQ. ID 24 encodes for a protein domain according to SEQ. ID 42, whereas the humanized light chain of an anti-CD123 scFv according to SEQ. ID 25 encodes for a protein domain according to SEQ. ID 43. The La 5B9 epitop according to SEQ. ID 14 encodes for a protein according to SEQ. ID 44. The nucleic acid sequence of the humanized heavy chain of an anti-CD33 scFv according to SEQ. ID 22 encodes for a protein domain according to SEQ. ID 41, whereas the humanized light chain of an anti-CD33 scFv according to SEQ. ID 21 encodes for a protein domain according to SEQ. ID 40.

The invention claimed is:

1. An antibody or fragment thereof that specifically binds CD33, wherein said antibody or antibody fragment comprises a single chain variable fragment (scFV) that comprises a humanized light chain variable domain comprising the amino acid sequence of SEQ ID NO:40 and a humanized heavy chain variable domain comprising the amino acid sequence of SEQ ID NO:41, wherein said light chain variable domain and said heavy chain variable domain are connected by a linker peptide that is about 10 to 25 amino acids in length.

2. The antibody or antibody fragment of claim 1 wherein the N-terminus of the amino acid sequence of SEQ ID NO:40 is connected to the C-terminus of the amino acid sequence of SEQ ID NO:41.

3. The antibody or antibody fragment of claim 1 wherein said linker peptide comprises the amino acid sequence of amino acids 413-427 of SEQ ID NO. 32.

4. The antibody or antibody fragment of claim 1 further comprising a second scFV against a second antigen.

5. A nucleic acid encoding the antibody or antibody fragment of claim 1.

6. The nucleic acid of claim 5, comprising the nucleotide sequence of SEQ ID NO. 21 and the nucleotide sequence of SEQ ID NO. 22.

7. A pharmaceutical composition comprising the antibody or antibody fragment of claim 1 and a pharmaceutically acceptable excipient.

8. A pharmaceutical composition comprising the antibody or antibody fragment of claim 4 and a pharmaceutically acceptable excipient.

9. The antibody or antibody fragment of claim 1 wherein said linker peptide comprises the amino acid sequence of amino acids 135-159 of SEQ ID NO. 30.

* * * * *

SEQUENCE LISTING

```
<160> NUMBER OF SEQ ID NOS: 44

<210> SEQ ID NO 1
<211> LENGTH: 2685
<212> TYPE: DNA
<213> ORGANISM: Artificial Sequence
<220> FEATURE:
<223> OTHER INFORMATION: Chimeric DNA Sequence mouse/human

<400> SEQUENCE: 1
atgcgccgca tgcagctgct gcttctgatc gctctgagcc tggctcttgt gaccaactct      60
gaattccagg tgcagctggt gcagagcgga gccgaggtga agaagcctgg agcctctgtg     120
aaggtgagct gcaaggcttc tggctacacc ttcacccact actacatcta ctgggtgaga     180
caggctcccg gacagggcct ggagtggatg ggaggcgtga accccagcaa cggaggcacc     240
cacttcaacg agaagttcaa gtctcgcgtg accatgaccc gcgacaccag catctctacc     300
gcttacatgg agctgagccg cctgcgctct gatgataccg ctgtgtacta ctgcgctcgc     360
agcgagtacg attacggact gggcttcgcc tactggggcc agggaaccct ggtgaccgtg     420
agctctggag gcggaggcag cggaggcggc ggatctggag gcggaggaag cgatatcgtg     480
atgacccagt ctcctgatag cctggctgtg agcctgggcg agagagctac catcaactgc     540
aagagcagcc agagcctgct gaactctcgc acccctaaga actaccttgc ttggtaccag     600
cagaagcctg gacagccccc taagctgctg atctactggg cttctacccg caagagcggc     660
gtgcccgaca gattctctgg cagcggaagc ggcaccgatt tcaccctgac catcagcagc     720
ctgcaggctg aggacgtggc cgtgtactac tgcaagcagt cttacaacct gctgaccttc     780
ggaggcggaa ccaaggtgga gatcaaggct gccgctctgg agaaggaggc cctgaagaag     840
atcatcgagg atcagcagga ggctctgaac aagtgggctg ccgctgggcc cggaggaggc     900
ggcagcaaga tcctggtcaa acagtcccct atgctggtcg cttacgacaa cgccgttaat     960
ctgagttgca aatatagtta caacctgttt agccgggaat tcgcgcatc tctccacaag    1020 ggactggatt ctgcggttga ggtttgtgtg gtctatggca attatagcca gcaactgcaa    1080
gtgtacagca aaacaggctt taactgcgac gggaaactcg gaacgaatc agtgaccttc    1140 tatctgcaga acctgtacgt taaccaaaca gatatttact tctgcaagat agaggtgatg    1200
gctccaccgc cagcactgga taacgagaag tccaatggaa ccatcattca cgtcaagggg    1260
aagcatctgt gtccttcccc gttgttccct gggccgagca aacccttttg ggtgcttgtg    1320
gtagttggcg gggtattggc ctgctattcc cttctcgtaa ctgtggcctt catcatcttc    1380
tgggtcagat ctaagaggtc tagggcggg catagcgact acatgaacat gacacccagg    1440
cggcctggcc ccactcgcaa acactaccag ccatacgcac caccaagaga ctttgccgca    1500
tatcggagtg gtggcggcgg gtcaggaggt ggagctagcg gtggaggagg ttccttctct    1560
```

```
aggtcagctg atgctcccgc ctatcagcaa ggtcagaacc agctctacaa tgagctgaat    1620
ctgggacgtc gggaggagta cgacgtgctg gataaacgaa gaggacgcga tcccgagatg    1680
ggtgggaagc ctaggcgcaa gaatccccag gaaggcctct acaatgaact gcagaaagac    1740
aagatggccg aagcctacag cgagattggc atgaaagggg agcgacggag aggaaaggga    1800
catgacgggt tgtatcaggg tcttttccact gcgacaaagg ataccatgg ggctctgcac    1860 atgcaagcac tgccacctag aggatccggc tcgagcggtg agggcagagg aagtcttcta    1920
acatgcggtg acgtggagga gaatcccggc ccaccggtcg ccaccatggt gagcaagggc    1980
gaggagctgt tcaccggggt ggtgcccatc ctggtcgagc tggacggcga cgtaaacggc    2040
cacaagttca gcgtgtccgg cgagggcgag ggcgatgcca cctacggcaa gctgaccctg    2100
aagttcatct gcaccaccgg caagctgccc gtgccctggc ccaccctcgt gaccaccctg    2160
acctacggcg tgcagtgctt cagccgctac cccgaccaca tgaagcagca cgacttcttc    2220
aagtccgcca tgcccgaagg ctacgtccag gagcgcacca tcttcttcaa ggacgacggc    2280
aactacaaga cccgcgccga ggtgaagttc gagggcgaca ccctggtgaa ccgcatcgag    2340
ctgaagggca tcgacttcaa ggaggacggc aacatcctgg ggcacaagct ggagtacaac    2400
tacaacagcc acaacgtcta tatcatggcc gacaagcaga agaacggcat caaggtgaac    2460
ttcaagatcc gccacaacat cgaggacggc agcgtgcagc tcgccgacca ctaccagcag    2520
aacaccccca tcggcgacgg ccccgtgctg ctgcccgaca ccactacct gagcacccag    2580 tccgccctga gcaaagaccc caacgagaag cgcgatcaca tggtcctgct ggagttcgtg    2640
accgccgccg ggatcactct cggcatggac gagctgtaca agtaa             2685

<210> SEQ ID NO 2
<211> LENGTH: 60
<212> TYPE: DNA
<213> ORGANISM: Homo sapiens

<400> SEQUENCE: 2
atgcgccgca tgcagctgct gcttctgatc gctctgagcc tggctcttgt gaccaactct     60

<210> SEQ ID NO 3
<211> LENGTH: 360
<212> TYPE: DNA
<213> ORGANISM: mouse

<400> SEQUENCE: 3
caggtgcagc tggtgcagag cggagccgag gtgaagaagc ctggagcctc tgtgaaggtg     60
agctgcaagg cttctggcta caccttcacc cactactaca tctactgggt gagacaggct    120
cccggacagg gcctggagtg gatgggaggc gtgaacccca gcaacggagg cacccacttc    180
aacgagaagt tcaagtctcg cgtgaccatg acccgcgaca ccagcatctc taccgcttac    240
atggagctga gccgcctgcg ctctgatgat accgctgtgt actactgcgc tcgcagcgag    300
tacgattacg gactgggctt cgcctactgg ggccagggaa ccctggtgac cgtgagctct    360

<210> SEQ ID NO 4
<211> LENGTH: 336
<212> TYPE: DNA
<213> ORGANISM: mouse

<400> SEQUENCE: 4
gatatcgtga tgacccagtc tcctgatagc ctggctgtga gcctgggcga gagagctacc     60
atcaactgca agagcagcca gagcctgctg aactctcgca cccctaagaa ctaccttgct    120
```

```
tggtaccagc agaagcctgg acagccccct aagctgctga tctactgggc ttctacccgc    180
aagagcggcg tgcccgacag attctctggc agcggaagcg gcaccgattt caccctgacc    240
atcagcagcc tgcaggctga ggacgtggcc gtgtactact gcaagcagtc ttacaacctg    300
ctgaccttcg gaggcggaac caaggtggag atcaag                               336

<210> SEQ ID NO 5
<211> LENGTH: 60
<212> TYPE: DNA
<213> ORGANISM: Homo sapiens

<400> SEQUENCE: 5
ctggagaagg aggccctgaa gaagatcatc gaggatcagc aggaggctct gaacaagtgg     60

<210> SEQ ID NO 6
<211> LENGTH: 399
<212> TYPE: DNA
<213> ORGANISM: Homo sapiens

<400> SEQUENCE: 6
aagatcctgg tcaaacagtc ccctatgctg gtcgcttacg acaacgccgt taatctgagt     60
tgcaaatata gttacaacct gtttagccgg gaatttcgcg catctctcca caagggactg    120
gattctgcgg ttgaggtttg tgtggtctat ggcaattata ccagcaact gcaagtgtac     180 agcaaaacag gctttaactg cgacgggaaa ctcgggaacg aatcagtgac cttctatctg    240
cagaacctgt acgttaacca aacagatatt tacttctgca agatagaggt gatggctcca    300
ccgccagcac tggataacga aagtccaat ggaaccatca ttcacgtcaa ggggaagcat     360
ctgtgtcctt ccccgttgtt ccctgggccg agcaaaccc                            399

<210> SEQ ID NO 7
<211> LENGTH: 81
<212> TYPE: DNA
<213> ORGANISM: Homo sapiens

<400> SEQUENCE: 7
ttttgggtgc ttgtggtagt tggcggggta ttggcctgct attcccttct cgtaactgtg     60
gccttcatca tcttctgggt c                                                81

<210> SEQ ID NO 8
<211> LENGTH: 123
<212> TYPE: DNA
<213> ORGANISM: Homo sapiens

<400> SEQUENCE: 8
agatctaaga ggtctagggg cgggcatagc gactacatga acatgacacc caggcggcct     60
ggccccactc gcaaacacta ccagccatac gcaccaccaa gagactttgc cgcatatcgg    120
agt                                                                   123

<210> SEQ ID NO 9
<211> LENGTH: 327
<212> TYPE: DNA
<213> ORGANISM: Homo sapiens

<400> SEQUENCE: 9
ttctctaggt cagctgatgc tcccgcctat cagcaaggtc agaaccagct ctacaatgag     60
ctgaatctgg gacgtcggga ggagtacgac gtgctggata acgaagagg acgcgatccc    120
```

```
gagatgggtg ggaagcctag gcgcaagaat ccccaggaag gcctctacaa tgaactgcag    180
aaagacaaga tggccgaagc ctacagcgag attggcatga aggggagcg acggagagga    240 aagggacatg acgggttgta tcagggtctt tccactgcga caaaggatac ctatggggct    300
ctgcacatgc aagcactgcc acctaga                                        327

<210> SEQ ID NO 10
<211> LENGTH: 981
<212> TYPE: DNA
<213> ORGANISM: Artificial Sequence
<220> FEATURE:
<223> OTHER INFORMATION: Chimeric DNA sequence mouse/human

<400> SEQUENCE: 10
atggagacag acacactcct gctatgggta ctgctgctct gggttccagg ttccactggt     60
gacgcggccc agccggccgg atccgatatc cagatgactc aaagtcctag ttccctgtct    120
gcatcagtgg gagaccgggt gaccattaca tgcggtacat cccaagacat caataattat    180
ctcaactggt atcagcagaa gccagcaaa gttcctaagt tattaatcta ctacacatcc    240
aggctgcatt ccggggtgcc ctcccgcttt tcgggctccg ggtcgggaac cgactttacc    300
ctaaccatat cttccctgca gcctgaagac gttgcaacga ctattgtca gcagtcaaag    360 acattaccat ggacatttgg tggtgggacg caactcactg tacttggtgg aggtggcagt    420
ggtggaggag ggagcggagc aagtgccgct ggaggcggag gttcaggcgg tggtggaagc    480
caggtgcagc tagtggagtc cggtggcggc ctcgttaagc cgggcggatc gctgcgcctt    540
tcatgtgccg catcaggatt cacattctcc agttactcta tgtcatggat tcggcaggca    600
cctggcaagg gattggaatg ggtctcgtac attaatgatt caggtggaag tacattctat    660
ccggacacgt taaaggtag atttaccatc agccgtgata cgcgaagaa tagcttgtac    720 ttacagatga atagcctgcg tgcagaggat actgctgtat attattgcgc tcgacgtatg    780
tattatggca atagtcactg gcactttgac gtctggggcc agggcacgac agttactgtc    840
tcttcgggag gaggaggatc cgcggccgct aaacccctac ctgaagtgac tgatgagtat    900
gctcgaggag ggcccgaaca aaaactcatc tcagaagagg atctgaatag cgccgtcgac    960
catcatcatc atcatcattg a                                              981

<210> SEQ ID NO 11
<211> LENGTH: 63
<212> TYPE: DNA
<213> ORGANISM: Homo sapiens

<400> SEQUENCE: 11
atggagacag acacactcct gctatgggta ctgctgctct gggttccagg ttccactggt     60
gac                                                                   63

<210> SEQ ID NO 12
<211> LENGTH: 321
<212> TYPE: DNA
<213> ORGANISM: mouse

<400> SEQUENCE: 12
gatatccaga tgactcaaag tcctagttcc ctgtctgcat cagtgggaga ccgggtgacc     60
attacatgcg gtacatccca agacatcaat aattatctca actggtatca gcagaagcca    120
ggcaaagttc ctaagttatt aatctactac acatccaggc tgcattccgg ggtgccctcc    180
cgcttttcgg gctccgggtc gggaaccgac tttaccctaa ccatatcttc cctgcagcct    240
```

```
gaagacgttg caacgtacta ttgtcagcag tcaaagacat taccatggac atttggtggt    300
gggacgcaac tcactgtact t                                              321

<210> SEQ ID NO 13
<211> LENGTH: 366
<212> TYPE: DNA
<213> ORGANISM: mouse

<400> SEQUENCE: 13
caggtgcagc tagtggagtc cggtggcggc ctcgttaagc cgggcggatc gctgcgcctt     60
tcatgtgccg catcaggatt cacattctcc agttactcta tgtcatggat tcggcaggca    120
cctggcaagg gattggaatg ggtctcgtac attaatgatt caggtggaag tacattctat    180
ccggacacgt taaaggtag atttaccatc agccgtgata cgcgaagaa tagcttgtac      240 ttacagatga atagcctgcg tgcagaggat actgctgtat attattgcgc tcgacgtatg    300
tattatggca atagtcactg gcactttgac gtctggggcc agggcacgac agttactgtc    360
tcttcg                                                               366

<210> SEQ ID NO 14
<211> LENGTH: 30
<212> TYPE: DNA
<213> ORGANISM: Homo sapiens

<400> SEQUENCE: 14 aaaccctac ctgaagtgac tgatgagtat                                       30

<210> SEQ ID NO 15
<211> LENGTH: 30
<212> TYPE: DNA
<213> ORGANISM: Homo sapiens

<400> SEQUENCE: 15
gaacaaaaac tcatctcaga agaggatctg                                      30

<210> SEQ ID NO 16
<211> LENGTH: 18
<212> TYPE: DNA
<213> ORGANISM: Homo sapiens

<400> SEQUENCE: 16
catcatcatc atcatcat                                                   18

<210> SEQ ID NO 17
<211> LENGTH: 909
<212> TYPE: DNA
<213> ORGANISM: Artificial Sequence
<220> FEATURE:
<223> OTHER INFORMATION: chimeric DNA construct human/mouse

<400> SEQUENCE: 17
atggagacag acacactcct gctatgggta ctgctgctct ggttccagg ttccactggt       60 gacgcggccc agccggccga ggtgcagctg cagcagtcag gacctgaact ggtgaagcct    120
gggacttcag tgaggatatc ctgcaagact tctggataca cattcactga atataccata    180
cactgggtga agcagagcca tggaaagagc cttgagtgga ttggaaacat caatcctaac    240
aatggtggta ccacctacaa tcagaagttc gaggacaagg ccacattgac tgtagacaag    300
tcctccagta cagcctacat ggagctccgc agcctaacat ctgaggattc tgcagtctat    360
```

```
tattgtgcag ctggttggaa cttttgactac tggggccaag ggaccacggt caccgtctcc      420
tcaggtggag gtggatcagg tggaggtgga tctggtggag gtggatctga cattgtgatg      480
acccagtctc acaaattcat gtccacatca gtaggagaca gggtcagcat catctgtaag      540
gccagtcaag atgtgggtac tgctgtagac tggtatcaac agaaaccagg acaatctcct      600
aaactactga tttattgggc atccactcgg cacactggag tccctgatcg cttcacaggc      660
agtggatctg gacagactt cactctcacc attactaatg ttcagtctga agacttggca       720
gattatttct gtcagcaata taacagctat ccccctcacgt tcggtgctgg gaccatgctg     780
gacctgaaag cggccgctaa acccctacct gaagtgactg atgagtatgc tcgaggaggg      840
cccgaacaaa aactcatctc agaagaggat ctgaatagcg ccgtcgacca tcatcatcat      900
catcattga                                                              909

<210> SEQ ID NO 18
<211> LENGTH: 345
<212> TYPE: DNA
<213> ORGANISM: mouse

<400> SEQUENCE: 18
gaggtgcagc tgcagcagtc aggacctgaa ctggtgaagc ctgggacttc agtgaggata      60
tcctgcaaga cttctggata cacattcact gaatatacca tacactgggt gaagcagagc     120 catgaaaga gccttgagtg gattggaaac atcaatccta acaatggtgg taccacctac       180
aatcagaagt tcgaggacaa ggccacattg actgtagaca gtcctccag tacagcctac       240 atggagctcc gcagcctaac atctgaggat tctgcagtct attattgtgc agctggttgg      300
aactttgact actggggcca agggaccacg gtcaccgtct cctca                      345

<210> SEQ ID NO 19
<211> LENGTH: 321
<212> TYPE: DNA
<213> ORGANISM: mouse

<400> SEQUENCE: 19
gacattgtga tgacccagtc tcacaaattc atgtccacat cagtaggaga cagggtcagc      60
atcatctgta aggccagtca agatgtgggt actgctgtag actggtatca acagaaacca     120
ggacaatctc ctaaaactact gatttattgg gcatccactc ggcacactgg agtccctgat    180
cgcttcacag gcagtggatc tgggacagac ttcactctca ccattactaa tgttcagtct    240
gaagacttgg cagattattt ctgtcagcaa tataacagct atccccctcac gttcggtgct    300 gggaccatgc tggacctgaa a                                                321

<210> SEQ ID NO 20
<211> LENGTH: 972
<212> TYPE: DNA
<213> ORGANISM: Artificial Sequence
<220> FEATURE:
<223> OTHER INFORMATION: chimeric DNA sequnece mouse/human

<400> SEQUENCE: 20
atggagacag acacactcct gctatgggta ctgctgctct ggttccagg ttccactggt       60 gacgcggccc agccggccgg atccgatata gttttaaccc aatcccctgc tagtctggcc     120
gtatccccag ccagagggc tactataacc tgcactgcaa gctcatctgt caactacatc      180
cattggtacc agcagaaacc tggacaaccg ccgaaacttc tgatatacga caccagcaag     240
gtcgcgtccg gggtgcctgc tcgattcagc ggcagcggat caggtactga cttcactttg     300
```

```
actatcaatc cagtggaagc gaacgatact gcgaactact actgccagca atggaggtcg      360
taccccttga catttggcca aggtactaaa ctagagataa aggtggaggt ggcagtggt       420 ggaggaggga gcggagcaag tggcgccgga ggcggaggtt caggcggtgg tggaagccag      480
gtacaactgg tccaatctgg agccgaagtc aagaaaccag gagcttctgt gaaagtcagt      540
tgcaaggcgt ctgggtatac attcacagat tacgtagtac actgggttag caagctcct      600 ggtcaagggc ttgaatggat gggatatatt aatccgtaca cgacggaac aaaatataac      660 gagaagttta agggtagagt aactatgacc agggacacaa gcatcagtac agcgtatatg      720
gaactgagtc gtctccggtc tgatgacacc gctgtctatt attgtgcaag agattaccgt      780
tacgaggttt acggcatgga ctattggggc caaggcactc tcgttaccgt gtcaagcgga      840
ggaggaggat ccgcggccgc taaacccta cctgaagtga ctgatgagta tgctcgagga      900
gggcccgaac aaaaactcat ctcagaagag gatctgaata gcgccgtcga ccatcatcat      960
catcatcatt ga                                                         972

<210> SEQ ID NO 21
<211> LENGTH: 318
<212> TYPE: DNA
<213> ORGANISM: mouse

<400> SEQUENCE: 21
gatatagttt aacccaatc ccctgctagt ctggccgtat ccccaggcca gagggctact      60
ataacctgca ctgcaagctc atctgtcaac tacatccatt ggtaccagca gaaacctgga      120
caaccgccga aacttctgat atacgacacc agcaaggtcg cgtccggggt gcctgctcga      180
ttcagcggca gcggatcagg tactgacttc actttgacta tcaatccagt ggaagcgaac      240
gatactgcga actactactg ccagcaatgg aggtcgtacc ccttgacatt tggccaaggt      300
actaaactag agataaaa                                                    318

<210> SEQ ID NO 22
<211> LENGTH: 360
<212> TYPE: DNA
<213> ORGANISM: mouse

<400> SEQUENCE: 22
caggtacaac tggtccaatc tggagccgaa gtcaagaaac caggagcttc tgtgaaagtc      60
agttgcaagg cgtctgggta tacattcaca gattacgtag tacactgggt taggcaagct      120
cctggtcaag gcttgaatg gatgggatat attaatccgt acaacgacgg aacaaaatat      180
aacgagaagt ttaagggtag agtaactatg accagggaca caagcatcag tacagcgtat      240
atggaactga gtcgtctccg gtctgatgac accgctgtct attattgtgc aagagattac      300
cgttacgagg tttacggcat ggactattgg ggccaaggca ctctcgttac cgtgtcaagc      360

<210> SEQ ID NO 23
<211> LENGTH: 963
<212> TYPE: DNA
<213> ORGANISM: Artificial Sequence
<220> FEATURE:
<223> OTHER INFORMATION: chimeric DNA sequence mouse/human

<400> SEQUENCE: 23
atggagacag acacactcct gctatgggta ctgctgctct ggttccaggt tccactggt       60 gacgcggccc agccggccga agtgcagctg cagcagtctg gccccgagct ggtcaaacca      120
```

| | | |
|---|---|---|
| ggcgccagcg tgaagatgag ctgcaaggcc agcggctaca ccttcaccga ctactacatg | 180 |
| aagtgggtca agcagagcca cggcaagagc ctggaatgga tcggcgacat catccccagc | 240 |
| aacggcgcca ccttctacaa ccagaagttc aagggcaagg ccaccctgac cgtggacaga | 300 |
| agcagcagca ccgcctacat gcacctgaac agcctgacca gcgaggacag cgccgtgtac | 360 |
| tactgcacca gaagccatct gctgcgggcc agttggttcg cttattgggg ccagggcacc | 420 |
| ctggtcacag tgtctgccgc ctctggagga ggaggtagtg gcggaggtgg gtccggtggc | 480 |
| ggtggctctg acttcgtgat gacccagagc cctagcagcc tgaccgtgac agccggcgag | 540 |
| aaagtgacca tgagctgcaa gagcagccag agcctgctga actccggcaa ccagaagaac | 600 |
| tacctgacct ggtatctgca gaagcccgga cagccccca agctgctgat ctactgggcc | 660 |
| agcaccagag aaagcggcgt gcccgataga ttcacaggca gcggcagcgg caccgacttc | 720 |
| accctgacaa tcagcagcgt gcaggccgag gacctggccg tgtactattg ccagaacgac | 780 |
| tacagctacc cctacacctt cggaggcggg accaagctgg aaatcaaggg aggaggagga | 840 |
| tccgcggccg ctaaacccct acctgaagtg actgatgagt atgctcgagg agggcccgaa | 900 |
| caaaaactca tctcagaaga ggatctgaat agcgccgtcg accatcatca tcatcatcat | 960 |
| tga | 963 |

<210> SEQ ID NO 24
<211> LENGTH: 357
<212> TYPE: DNA
<213> ORGANISM: mouse

<400> SEQUENCE: 24

| | | |
|---|---|---|
| gaagtgcagc tgcagcagtc tggcccccgag ctggtcaaac caggcgccag cgtgaagatg | 60 |
| agctgcaagg ccagcggcta caccttcacc gactactaca tgaagtgggt caagcagagc | 120 |
| cacggcaaga gcctggaatg gatcggcgac atcatcccca gcaacggcgc caccttctac | 180 |
| aaccagaagt tcaagggcaa ggccaccctg accgtggaca gaagcagcag caccgcctac | 240 |
| atgcacctga cagcctgac cagcgaggac agcgccgtgt actactgcac cagaagccat | 300 |
| ctgctgcggg ccagttggtt cgcttattgg ggccagggca ccctggtcac agtgtct | 357 |

<210> SEQ ID NO 25
<211> LENGTH: 339
<212> TYPE: DNA
<213> ORGANISM: mouse

<400> SEQUENCE: 25

| | | |
|---|---|---|
| gacttcgtga tgacccagag ccctagcagc ctgaccgtga cagccggcga gaaagtgacc | 60 |
| atgagctgca agagcagcca gagcctgctg aactccggca accagaagaa ctacctgacc | 120 |
| tggtatctgc agaagcccgg acagccccca agctgctga tctactgggc cagcaccaga | 180 |
| gaaagcggcg tgcccgatag attcacaggc agcggcagcg gcaccgactt caccctgaca | 240 |
| atcagcagcg tgcaggccga ggacctggcc gtgtactatt gccagaacga ctacagctac | 300 |
| ccctacacct tcggaggcgg gaccaagctg gaaatcaag | 339 |

<210> SEQ ID NO 26
<211> LENGTH: 1671
<212> TYPE: DNA
<213> ORGANISM: Artificial Sequence
<220> FEATURE:
<223> OTHER INFORMATION: chimeric DNA sequnece mouse/human

<400> SEQUENCE: 26

```
atggagacag acacactcct gctatgggta ctgctgctct gggttccagg ttccactggt    60
gacgcggccc agccggccga agtgcagctg cagcagtctg gccccgagct ggtcaaacca   120
ggcgccagcg tgaagatgag ctgcaaggcc agcggctaca ccttcaccga ctactacatg   180
aagtgggtca agcagagcca cggcaagagc ctggaatgga tcggcgacat catccccagc   240
aacggcgcca ccttctacaa ccagaagttc aagggcaagg ccaccctgac cgtggacaga   300
agcagcagca ccgcctacat gcacctgaac agcctgacca cgaggacagc gccgtgtac    360
tactgcacca gaagccatct gctgcgggcc agttggttcg cttattgggg ccagggcacc   420
ctggtcacag tgtctgccgc tctggagga ggaggtagtg gcggaggtgg gtccggtggc    480
ggtggctctg acttcgtgat gacccagagc cctagcagcc tgaccgtgac agccggcgag   540
aaagtgacca tgagctgcaa gagcagccag agcctgctga actccggcaa ccagaagaac   600
tacctgacct ggtatctgca gaagcccgga cagccccca agctgctgat ctactgggcc   660
agcaccagag aaagcggcgt gcccgataga ttcacaggca gcggcagcgg caccgacttc   720
accctgacaa tcagcagcgt gcaggccgag gacctggccg tgtactattg ccagaacgac   780
tacagctacc cctacacctt cggaggcggg accaagctgg aaatcaaggc ggccgctaaa   840
ccccctacctg aagtgactga tgagtatgct cgaggacagg tacaactggt ccaatctgga   900
gccgaagtca agaaaccagg agcttctgtg aaagtcagtt gcaaggcgtc tgggtataca   960
ttcacagatt acgtagtaca ctgggttagg caagctcctg gtcaagggct tgaatggatg  1020
ggatatatta atccgtacaa cgacggaaca aaatataacg agaagtttaa gggtagagta  1080
actatgacca gggacacaag catcagtaca gcgtatatgg aactgagtcg tctccggtct  1140
gatgacaccg ctgtctatta ttgtgcaaga gattaccgtt acgagtttta cggcatggac  1200
tattggggcc aaggcactct cgttaccgtg tcaagcggcg gcggcggatc cggcggtggc  1260
ggttccggag gaggcggatc cgatatagtt ttaacccaat cccctgctag tctggccgta  1320
tccccaggcc agagggctac tataacctgc actgcaagct catctgtcaa ctacatccat  1380
tggtaccagc agaaacctgg acaaccgccg aaacttctga tatacgacac cagcaaggtc  1440
gcgtccgggg tgcctgctcg attcagcggc agcggatcag gtactgactt cactttgact  1500
atcaatccag tggaagcgaa cgatactgcg aactactact gccagcaatg gaggtcgtac  1560
cccttgacat ttggccaagg tactaaacta gagataaaag ggcccgaaca aaaactcatc  1620
tcagaagagg atctgaatag cgccgtcgac catcatcatc atcatcattg a           1671
```

<210> SEQ ID NO 27
<211> LENGTH: 894
<212> TYPE: PRT
<213> ORGANISM: Artificial Sequence
<220> FEATURE:
<223> OTHER INFORMATION: chimeric fusion protein mouse/human

<400> SEQUENCE: 27

Met Arg Arg Met Gln Leu Leu Leu Ile Ala Leu Ser Leu Ala Leu
1               5                   10                  15

Val Thr Asn Ser Glu Phe Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr His Tyr Ile Tyr Trp Val Arg Gln Ala Pro Gly
    50                  55                  60

```
Gln Gly Leu Glu Trp Met Gly Gly Val Asn Pro Ser Asn Gly Gly Thr
 65                  70                  75                  80

His Phe Asn Glu Lys Phe Lys Ser Arg Val Thr Met Thr Arg Asp Thr
                 85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Ser Glu Tyr Asp Tyr Gly Leu Gly
        115                 120                 125

Phe Ala Tyr Trp Gly Gln Gly Thr Leu Val Thr Val Ser Ser Gly Gly
    130                 135                 140

Gly Gly Ser Gly Gly Gly Ser Gly Gly Gly Ser Asp Ile Val
145                 150                 155                 160

Met Thr Gln Ser Pro Asp Ser Leu Ala Val Ser Leu Gly Glu Arg Ala
                165                 170                 175

Thr Ile Asn Cys Lys Ser Ser Gln Ser Leu Leu Asn Ser Arg Thr Pro
            180                 185                 190

Lys Asn Tyr Leu Ala Trp Tyr Gln Gln Lys Pro Gly Gln Pro Pro Lys
        195                 200                 205

Leu Leu Ile Tyr Trp Ala Ser Thr Arg Lys Ser Gly Val Pro Asp Arg
    210                 215                 220

Phe Ser Gly Ser Gly Ser Gly Thr Asp Phe Thr Leu Thr Ile Ser Ser
225                 230                 235                 240

Leu Gln Ala Glu Asp Val Ala Val Tyr Tyr Cys Lys Gln Ser Tyr Asn
                245                 250                 255

Leu Leu Thr Phe Gly Gly Gly Thr Lys Val Glu Ile Lys Ala Ala Ala
            260                 265                 270

Leu Glu Lys Glu Ala Leu Lys Lys Ile Ile Glu Asp Gln Gln Glu Ala
        275                 280                 285

Leu Asn Lys Trp Ala Ala Ala Gly Pro Gly Gly Gly Ser Lys Ile
    290                 295                 300

Leu Val Lys Gln Ser Pro Met Leu Val Ala Tyr Asp Asn Ala Val Asn
305                 310                 315                 320

Leu Ser Cys Lys Tyr Ser Tyr Asn Leu Phe Ser Arg Glu Phe Arg Ala
                325                 330                 335

Ser Leu His Lys Gly Leu Asp Ser Ala Val Glu Val Cys Val Val Tyr
            340                 345                 350

Gly Asn Tyr Ser Gln Gln Leu Gln Val Tyr Ser Lys Thr Gly Phe Asn
        355                 360                 365

Cys Asp Gly Lys Leu Gly Asn Glu Ser Val Thr Phe Tyr Leu Gln Asn
    370                 375                 380

Leu Tyr Val Asn Gln Thr Asp Ile Tyr Phe Cys Lys Ile Glu Val Met
385                 390                 395                 400

Ala Pro Pro Pro Ala Leu Asp Asn Glu Lys Ser Asn Gly Thr Ile Ile
                405                 410                 415

His Val Lys Gly Lys His Leu Cys Pro Ser Pro Leu Phe Pro Gly Pro
            420                 425                 430

Ser Lys Pro Phe Trp Val Leu Val Val Gly Gly Val Leu Ala Cys
        435                 440                 445

Tyr Ser Leu Leu Val Thr Val Ala Phe Ile Ile Phe Trp Val Arg Ser
    450                 455                 460

Lys Arg Ser Arg Gly Gly His Ser Asp Tyr Met Asn Met Thr Pro Arg
465                 470                 475                 480

Arg Pro Gly Pro Thr Arg Lys His Tyr Gln Pro Tyr Ala Pro Pro Arg
```

```
            485                 490                 495
Asp Phe Ala Ala Tyr Arg Ser Gly Gly Gly Ser Gly Gly Ala
            500                 505                 510

Ser Gly Gly Gly Ser Phe Ser Arg Ser Ala Asp Ala Pro Ala Tyr
        515                 520                 525

Gln Gln Gly Gln Asn Gln Leu Tyr Asn Glu Leu Asn Leu Gly Arg Arg
        530                 535                 540

Glu Glu Tyr Asp Val Leu Asp Lys Arg Gly Arg Asp Pro Glu Met
545                 550                 555                 560

Gly Gly Lys Pro Arg Arg Lys Asn Pro Gln Glu Gly Leu Tyr Asn Glu
                565                 570                 575

Leu Gln Lys Asp Lys Met Ala Glu Ala Tyr Ser Glu Ile Gly Met Lys
                580                 585                 590

Gly Glu Arg Arg Arg Gly Lys Gly His Asp Gly Leu Tyr Gln Gly Leu
                595                 600                 605

Ser Thr Ala Thr Lys Asp Thr Tyr Gly Ala Leu His Met Gln Ala Leu
                610                 615                 620

Pro Pro Arg Gly Ser Gly Ser Ser Gly Glu Gly Arg Gly Ser Leu Leu
625                 630                 635                 640

Thr Cys Gly Asp Val Glu Glu Asn Pro Gly Pro Val Ala Thr Met
                645                 650                 655

Val Ser Lys Gly Glu Glu Leu Phe Thr Gly Val Val Pro Ile Leu Val
                660                 665                 670

Glu Leu Asp Gly Asp Val Asn Gly His Lys Phe Ser Val Ser Gly Glu
                675                 680                 685

Gly Glu Gly Asp Ala Thr Tyr Gly Lys Leu Thr Leu Lys Phe Ile Cys
                690                 695                 700

Thr Thr Gly Lys Leu Pro Val Pro Trp Pro Thr Leu Val Thr Thr Leu
705                 710                 715                 720

Thr Tyr Gly Val Gln Cys Phe Ser Arg Tyr Pro Asp His Met Lys Gln
                725                 730                 735

His Asp Phe Phe Lys Ser Ala Met Pro Glu Gly Tyr Val Gln Glu Arg
                740                 745                 750

Thr Ile Phe Phe Lys Asp Asp Gly Asn Tyr Lys Thr Arg Ala Glu Val
                755                 760                 765

Lys Phe Glu Gly Asp Thr Leu Val Asn Arg Ile Glu Leu Lys Gly Ile
770                 775                 780

Asp Phe Lys Glu Asp Gly Asn Ile Leu Gly His Lys Leu Glu Tyr Asn
785                 790                 795                 800

Tyr Asn Ser His Asn Val Tyr Ile Met Ala Asp Lys Gln Lys Asn Gly
                805                 810                 815

Ile Lys Val Asn Phe Lys Ile Arg His Asn Ile Glu Asp Gly Ser Val
                820                 825                 830

Gln Leu Ala Asp His Tyr Gln Gln Asn Thr Pro Ile Gly Asp Gly Pro
                835                 840                 845

Val Leu Leu Pro Asp Asn His Tyr Leu Ser Thr Gln Ser Ala Leu Ser
850                 855                 860

Lys Asp Pro Asn Glu Lys Arg Asp His Met Val Leu Leu Glu Phe Val
865                 870                 875                 880

Thr Ala Ala Gly Ile Thr Leu Gly Met Asp Glu Leu Tyr Lys
                885                 890

<210> SEQ ID NO 28
```

<211> LENGTH: 326
<212> TYPE: PRT
<213> ORGANISM: Artificial Sequence
<220> FEATURE:
<223> OTHER INFORMATION: chimeric fusion protein mouse/human

<400> SEQUENCE: 28

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Gly Ser Asp Ile Gln Met
            20                  25                  30

Thr Gln Ser Pro Ser Ser Leu Ser Ala Ser Val Gly Asp Arg Val Thr
        35                  40                  45

Ile Thr Cys Gly Thr Ser Gln Asp Ile Asn Asn Tyr Leu Asn Trp Tyr
50                  55                  60

Gln Gln Lys Pro Gly Lys Val Pro Lys Leu Leu Ile Tyr Tyr Thr Ser
65                  70                  75                  80

Arg Leu His Ser Gly Val Pro Ser Arg Phe Ser Gly Ser Gly Ser Gly
                85                  90                  95

Thr Asp Phe Thr Leu Thr Ile Ser Ser Leu Gln Pro Glu Asp Val Ala
            100                 105                 110

Thr Tyr Tyr Cys Gln Gln Ser Lys Thr Leu Pro Trp Thr Phe Gly Gly
        115                 120                 125

Gly Thr Gln Leu Thr Val Leu Gly Gly Gly Gly Ser Gly Gly Gly Gly
130                 135                 140

Ser Gly Ala Ser Ala Ala Gly Gly Gly Ser Gly Gly Gly Gly Ser
145                 150                 155                 160

Gln Val Gln Leu Val Glu Ser Gly Gly Leu Val Lys Pro Gly Gly
                165                 170                 175

Ser Leu Arg Leu Ser Cys Ala Ala Ser Gly Phe Thr Phe Ser Ser Tyr
            180                 185                 190

Ser Met Ser Trp Ile Arg Gln Ala Pro Gly Lys Gly Leu Glu Trp Val
        195                 200                 205

Ser Tyr Ile Asn Asp Ser Gly Gly Ser Thr Phe Tyr Pro Asp Thr Val
210                 215                 220

Lys Gly Arg Phe Thr Ile Ser Arg Asp Asn Ala Lys Asn Ser Leu Tyr
225                 230                 235                 240

Leu Gln Met Asn Ser Leu Arg Ala Glu Asp Thr Ala Val Tyr Tyr Cys
                245                 250                 255

Ala Arg Arg Met Tyr Tyr Gly Asn Ser His Trp His Phe Asp Val Trp
            260                 265                 270

Gly Gln Gly Thr Thr Val Thr Val Ser Ser Gly Gly Gly Gly Ser Ala
        275                 280                 285

Ala Ala Lys Pro Leu Pro Glu Val Thr Asp Glu Tyr Ala Arg Gly Gly
290                 295                 300

Pro Glu Gln Lys Leu Ile Ser Glu Glu Asp Leu Asn Ser Ala Val Asp
305                 310                 315                 320

His His His His His His
            325
```

<210> SEQ ID NO 29
<211> LENGTH: 302
<212> TYPE: PRT
<213> ORGANISM: Artificial Sequence
<220> FEATURE:
<223> OTHER INFORMATION: chimeric fusion protein mouse/human

<400> SEQUENCE: 29

Met Glu Thr Asp Thr Leu Leu Leu Trp Val Leu Leu Leu Trp Val Pro
1               5                   10                  15

Gly Ser Thr Gly Asp Ala Ala Gln Pro Ala Glu Val Gln Leu Gln Gln
            20                  25                  30

Ser Gly Pro Glu Leu Val Lys Pro Gly Thr Ser Val Arg Ile Ser Cys
        35                  40                  45

Lys Thr Ser Gly Tyr Thr Phe Thr Glu Tyr Thr Ile His Trp Val Lys
    50                  55                  60

Gln Ser His Gly Lys Ser Leu Glu Trp Ile Gly Asn Ile Asn Pro Asn
65                  70                  75                  80

Asn Gly Gly Thr Thr Tyr Asn Gln Lys Phe Glu Asp Lys Ala Thr Leu
                85                  90                  95

Thr Val Asp Lys Ser Ser Ser Thr Ala Tyr Met Glu Leu Arg Ser Leu
            100                 105                 110

Thr Ser Glu Asp Ser Ala Val Tyr Tyr Cys Ala Ala Gly Trp Asn Phe
        115                 120                 125

Asp Tyr Trp Gly Gln Gly Thr Thr Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser His Lys Phe Met Ser Thr Ser Val Gly Asp Arg Val Ser
                165                 170                 175

Ile Ile Cys Lys Ala Ser Gln Asp Val Gly Thr Ala Val Asp Trp Tyr
            180                 185                 190

Gln Gln Lys Pro Gly Gln Ser Pro Lys Leu Leu Ile Tyr Trp Ala Ser
        195                 200                 205

Thr Arg His Thr Gly Val Pro Asp Arg Phe Thr Gly Ser Gly Ser Gly
    210                 215                 220

Thr Asp Phe Thr Leu Thr Ile Thr Asn Val Gln Ser Glu Asp Leu Ala
225                 230                 235                 240

Asp Tyr Phe Cys Gln Gln Tyr Asn Ser Tyr Pro Leu Thr Phe Gly Ala
                245                 250                 255

Gly Thr Met Leu Asp Leu Lys Ala Ala Ala Lys Pro Leu Pro Glu Val
            260                 265                 270

Thr Asp Glu Tyr Ala Arg Gly Gly Pro Glu Gln Lys Leu Ile Ser Glu
        275                 280                 285

Glu Asp Leu Asn Ser Ala Val Asp His His His His His
    290                 295                 300

<210> SEQ ID NO 30
<211> LENGTH: 323
<212> TYPE: PRT
<213> ORGANISM: Artificial Sequence
<220> FEATURE:
<223> OTHER INFORMATION: chimeric construct

<400> SEQUENCE: 30

Met Glu Thr Asp Thr Leu Leu Leu Trp Val Leu Leu Leu Trp Val Pro
1               5                   10                  15

Gly Ser Thr Gly Asp Ala Ala Gln Pro Ala Gly Ser Asp Ile Val Leu
            20                  25                  30

Thr Gln Ser Pro Ala Ser Leu Ala Val Ser Pro Gly Gln Arg Ala Thr
        35                  40                  45

Ile Thr Cys Thr Ala Ser Ser Ser Val Asn Tyr Ile His Trp Tyr Gln

```
                50                  55                  60
Gln Lys Pro Gly Gln Pro Pro Lys Leu Leu Ile Tyr Asp Thr Ser Lys
 65                  70                  75                  80

Val Ala Ser Gly Val Pro Ala Arg Phe Ser Gly Ser Gly Ser Gly Thr
                 85                  90                  95

Asp Phe Thr Leu Thr Ile Asn Pro Val Glu Ala Asn Asp Thr Ala Asn
                100                 105                 110

Tyr Tyr Cys Gln Gln Trp Arg Ser Tyr Pro Leu Thr Phe Gly Gln Gly
                115                 120                 125

Thr Lys Leu Glu Ile Lys Gly Gly Gly Ser Gly Gly Gly Gly Ser
            130                 135                 140

Gly Ala Ser Gly Ala Gly Gly Gly Ser Gly Gly Gly Gly Ser Gln
145                 150                 155                 160

Val Gln Leu Val Gln Ser Gly Ala Glu Val Lys Lys Pro Gly Ala Ser
                165                 170                 175

Val Lys Val Ser Cys Lys Ala Ser Gly Tyr Thr Phe Thr Asp Tyr Val
                180                 185                 190

Val His Trp Val Arg Gln Ala Pro Gly Gln Gly Leu Glu Trp Met Gly
                195                 200                 205

Tyr Ile Asn Pro Tyr Asn Asp Gly Thr Lys Tyr Asn Glu Lys Phe Lys
                210                 215                 220

Gly Arg Val Thr Met Thr Arg Asp Thr Ser Ile Ser Thr Ala Tyr Met
225                 230                 235                 240

Glu Leu Ser Arg Leu Arg Ser Asp Asp Thr Ala Val Tyr Tyr Cys Ala
                245                 250                 255

Arg Asp Tyr Arg Tyr Glu Val Tyr Gly Met Asp Tyr Trp Gly Gln Gly
                260                 265                 270

Thr Leu Val Thr Val Ser Ser Gly Gly Gly Ser Ala Ala Ala Lys
                275                 280                 285

Pro Leu Pro Glu Val Thr Asp Glu Tyr Ala Arg Gly Gly Pro Glu Gln
                290                 295                 300

Lys Leu Ile Ser Glu Glu Asp Leu Asn Ser Ala Val Asp His His His
305                 310                 315                 320

His His His

<210> SEQ ID NO 31
<211> LENGTH: 320
<212> TYPE: PRT
<213> ORGANISM: Artificial Sequence
<220> FEATURE:
<223> OTHER INFORMATION: chimeric fusion protein mouse/human

<400> SEQUENCE: 31

Met Glu Thr Asp Thr Leu Leu Leu Trp Val Leu Leu Leu Trp Val Pro
  1               5                  10                  15

Gly Ser Thr Gly Asp Ala Ala Gln Pro Ala Glu Val Gln Leu Gln Gln
                 20                  25                  30

Ser Gly Pro Glu Leu Val Lys Pro Gly Ala Ser Val Lys Met Ser Cys
                 35                  40                  45

Lys Ala Ser Gly Tyr Thr Phe Thr Asp Tyr Tyr Met Lys Trp Val Lys
             50                  55                  60

Gln Ser His Gly Lys Ser Leu Glu Trp Ile Gly Asp Ile Ile Pro Ser
 65                  70                  75                  80

Asn Gly Ala Thr Phe Tyr Asn Gln Lys Phe Lys Gly Lys Ala Thr Leu
                 85                  90                  95
```

Thr Val Asp Arg Ser Ser Ser Thr Ala Tyr Met His Leu Asn Ser Leu
            100                 105                 110

Thr Ser Glu Asp Ser Ala Val Tyr Tyr Cys Thr Arg Ser His Leu Leu
        115                 120                 125

Arg Ala Ser Trp Phe Ala Tyr Trp Gly Gln Gly Thr Leu Val Thr Val
    130                 135                 140

Ser Ala Ala Ser Gly Gly Gly Gly Ser Gly Gly Gly Ser Gly Gly
145                 150                 155                 160

Gly Gly Ser Asp Phe Val Met Thr Gln Ser Pro Ser Ser Leu Thr Val
                165                 170                 175

Thr Ala Gly Glu Lys Val Thr Met Ser Cys Lys Ser Ser Gln Ser Leu
            180                 185                 190

Leu Asn Ser Gly Asn Gln Lys Asn Tyr Leu Thr Trp Tyr Leu Gln Lys
        195                 200                 205

Pro Gly Gln Pro Pro Lys Leu Leu Ile Tyr Trp Ala Ser Thr Arg Glu
    210                 215                 220

Ser Gly Val Pro Asp Arg Phe Thr Gly Ser Gly Ser Gly Thr Asp Phe
225                 230                 235                 240

Thr Leu Thr Ile Ser Ser Val Gln Ala Glu Asp Leu Ala Val Tyr Tyr
                245                 250                 255

Cys Gln Asn Asp Tyr Ser Tyr Pro Tyr Thr Phe Gly Gly Gly Thr Lys
            260                 265                 270

Leu Glu Ile Lys Gly Gly Gly Ser Ala Ala Ala Lys Pro Leu Pro
        275                 280                 285

Glu Val Thr Asp Glu Tyr Ala Arg Gly Gly Pro Glu Gln Lys Leu Ile
    290                 295                 300

Ser Glu Glu Asp Leu Asn Ser Ala Val Asp His His His His His His
305                 310                 315                 320

<210> SEQ ID NO 32
<211> LENGTH: 556
<212> TYPE: PRT
<213> ORGANISM: Artificial Sequence
<220> FEATURE:
<223> OTHER INFORMATION: chimeric fusion protein mouse/human

<400> SEQUENCE: 32

Met Glu Thr Asp Thr Leu Leu Leu Trp Val Leu Leu Leu Trp Val Pro
1               5                   10                  15

Gly Ser Thr Gly Asp Ala Ala Gln Pro Ala Glu Val Gln Leu Gln Gln
            20                  25                  30

Ser Gly Pro Glu Leu Val Lys Pro Gly Ala Ser Val Lys Met Ser Cys
        35                  40                  45

Lys Ala Ser Gly Tyr Thr Phe Thr Asp Tyr Tyr Met Lys Trp Val Lys
    50                  55                  60

Gln Ser His Gly Lys Ser Leu Glu Trp Ile Gly Asp Ile Ile Pro Ser
65                  70                  75                  80

Asn Gly Ala Thr Phe Tyr Asn Gln Lys Phe Lys Gly Lys Ala Thr Leu
                85                  90                  95

Thr Val Asp Arg Ser Ser Ser Thr Ala Tyr Met His Leu Asn Ser Leu
            100                 105                 110

Thr Ser Glu Asp Ser Ala Val Tyr Tyr Cys Thr Arg Ser His Leu Leu
        115                 120                 125

Arg Ala Ser Trp Phe Ala Tyr Trp Gly Gln Gly Thr Leu Val Thr Val
    130                 135                 140

```
Ser Ala Ala Ser Gly Gly Gly Ser Gly Gly Gly Ser Gly Gly
145                 150                 155                 160

Gly Gly Ser Asp Phe Val Met Thr Gln Ser Pro Ser Ser Leu Thr Val
                165                 170                 175

Thr Ala Gly Glu Lys Val Thr Met Ser Cys Lys Ser Ser Gln Ser Leu
            180                 185                 190

Leu Asn Ser Gly Asn Gln Lys Asn Tyr Leu Thr Trp Tyr Leu Gln Lys
        195                 200                 205

Pro Gly Gln Pro Pro Lys Leu Leu Ile Tyr Trp Ala Ser Thr Arg Glu
    210                 215                 220

Ser Gly Val Pro Asp Arg Phe Thr Gly Ser Gly Ser Gly Thr Asp Phe
225                 230                 235                 240

Thr Leu Thr Ile Ser Ser Val Gln Ala Glu Asp Leu Ala Val Tyr Tyr
                245                 250                 255

Cys Gln Asn Asp Tyr Ser Tyr Pro Tyr Thr Phe Gly Gly Gly Thr Lys
            260                 265                 270

Leu Glu Ile Lys Ala Ala Ala Lys Pro Leu Pro Glu Val Thr Asp Glu
        275                 280                 285

Tyr Ala Arg Gly Gln Val Gln Leu Val Gln Ser Gly Ala Glu Val Lys
    290                 295                 300

Lys Pro Gly Ala Ser Val Lys Val Ser Cys Lys Ala Ser Gly Tyr Thr
305                 310                 315                 320

Phe Thr Asp Tyr Val Val His Trp Val Arg Gln Ala Pro Gly Gln Gly
                325                 330                 335

Leu Glu Trp Met Gly Tyr Ile Asn Pro Tyr Asn Asp Gly Thr Lys Tyr
            340                 345                 350

Asn Glu Lys Phe Lys Gly Arg Val Thr Met Thr Arg Asp Thr Ser Ile
        355                 360                 365

Ser Thr Ala Tyr Met Glu Leu Ser Arg Leu Arg Ser Asp Asp Thr Ala
    370                 375                 380

Val Tyr Tyr Cys Ala Arg Asp Tyr Arg Tyr Glu Val Tyr Gly Met Asp
385                 390                 395                 400

Tyr Trp Gly Gln Gly Thr Leu Val Thr Val Ser Ser Gly Gly Gly Gly
                405                 410                 415

Ser Gly Gly Gly Gly Ser Gly Gly Gly Gly Ser Asp Ile Val Leu Thr
            420                 425                 430

Gln Ser Pro Ala Ser Leu Ala Val Ser Pro Gly Gln Arg Ala Thr Ile
        435                 440                 445

Thr Cys Thr Ala Ser Ser Ser Val Asn Tyr Ile His Trp Tyr Gln Gln
    450                 455                 460

Lys Pro Gly Gln Pro Pro Lys Leu Leu Ile Tyr Asp Thr Ser Lys Val
465                 470                 475                 480

Ala Ser Gly Val Pro Ala Arg Phe Ser Gly Ser Gly Ser Gly Thr Asp
                485                 490                 495

Phe Thr Leu Thr Ile Asn Pro Val Glu Ala Asn Asp Thr Ala Asn Tyr
            500                 505                 510

Tyr Cys Gln Gln Trp Arg Ser Tyr Pro Leu Thr Phe Gly Gln Gly Thr
        515                 520                 525

Lys Leu Glu Ile Lys Gly Pro Glu Gln Lys Leu Ile Ser Glu Glu Asp
    530                 535                 540

Leu Asn Ser Ala Val Asp His His His His His
545                 550                 555
```

<210> SEQ ID NO 33
<211> LENGTH: 120
<212> TYPE: PRT
<213> ORGANISM: Mouse

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Ile Tyr Trp Val Arg Gln Ala Pro Gly Gln Gly Leu Glu Trp Met
        35                  40                  45

Gly Gly Val Asn Pro Ser Asn Gly Gly Thr His Phe Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Tyr Asp Tyr Gly Leu Gly Phe Ala Tyr Trp Gly Gln
            100                 105                 110

Gly Thr Leu Val Thr Val Ser Ser
        115                 120

<210> SEQ ID NO 34
<211> LENGTH: 112
<212> TYPE: PRT
<213> ORGANISM: mouse

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Pro Lys Asn Tyr Leu Ala Trp Tyr Gln Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gly Gly Thr Lys Val Glu Ile Lys
            100                 105                 110

<210> SEQ ID NO 35
<211> LENGTH: 20
<212> TYPE: PRT
<213> ORGANISM: Homo sapiens

<400> SEQUENCE: 35

Leu Glu Lys Glu Ala Leu Lys Lys Ile Ile Glu Asp Gln Gln Glu Ala
1               5                   10                  15

Leu Asn Lys Trp
            20

<210> SEQ ID NO 36
<211> LENGTH: 107
<212> TYPE: PRT

<213> ORGANISM: mouse

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gly Thr Ser Gln Asp Ile Asn Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ser Lys Thr Leu Pro Trp
                85                  90                  95

Thr Phe Gly Gly Gly Thr Gln Leu Thr Val Leu
            100                 105

<210> SEQ ID NO 37
<211> LENGTH: 122
<212> TYPE: PRT
<213> ORGANISM: mouse

<400> SEQUENCE: 37

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Ile Arg Gln Ala Pro Gly Lys Gly Leu Glu Trp Val
        35                  40                  45

Ser Tyr Ile Asn Asp Ser Gly Gly Ser Thr Phe Tyr Pro Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Met Tyr Tyr Gly Asn Ser His Trp His Phe Asp Val Trp
            100                 105                 110

Gly Gln Gly Thr Thr Val Thr Val Ser Ser
        115                 120

<210> SEQ ID NO 38
<211> LENGTH: 115
<212> TYPE: PRT
<213> ORGANISM: mouse

<400> SEQUENCE: 38

Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
50                  55                  60

Glu Asp Lys Ala Thr Leu Thr Val Asp Lys Ser Ser Ser Thr Ala Tyr
65                  70                  75                  80

```
Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 39
<211> LENGTH: 107
<212> TYPE: PRT
<213> ORGANISM: mouse

<400> SEQUENCE: 39

Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
            20                  25                  30

Val Asp Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Met Leu Asp Leu Lys
            100                 105

<210> SEQ ID NO 40
<211> LENGTH: 106
<212> TYPE: PRT
<213> ORGANISM: mouse

<400> SEQUENCE: 40

Asp Ile Val Leu Thr Gln Ser Pro Ala Ser Leu Ala Val Ser Pro Gly
1               5                   10                  15

Gln Arg Ala Thr Ile Thr Cys Thr Ala Ser Ser Ser Val Asn Tyr Ile
            20                  25                  30

His Trp Tyr Gln Gln Lys Pro Gly Gln Pro Pro Lys Leu Leu Ile Tyr
        35                  40                  45

Asp Thr Ser Lys Val Ala Ser Gly Val Pro Ala Arg Phe Ser Gly Ser
    50                  55                  60

Gly Ser Gly Thr Asp Phe Thr Leu Thr Ile Asn Pro Val Glu Ala Asn
65                  70                  75                  80

Asp Thr Ala Asn Tyr Tyr Cys Gln Gln Trp Arg Ser Tyr Pro Leu Thr
                85                  90                  95

Phe Gly Gln Gly Thr Lys Leu Glu Ile Lys
            100                 105

<210> SEQ ID NO 41
<211> LENGTH: 120
<212> TYPE: PRT
<213> ORGANISM: mouse

<400> SEQUENCE: 41

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Tyr
            20                  25                  30

Val Val His Trp Val Arg Gln Ala Pro Gly Gln Gly Leu Glu Trp Met
            35                  40                  45

Gly Tyr Ile Asn Pro Tyr Asn Asp Gly Thr Lys Tyr Asn Glu Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Leu Val Thr Val Ser Ser
            115                 120
```

<210> SEQ ID NO 42
<211> LENGTH: 119
<212> TYPE: PRT
<213> ORGANISM: mouse

<400> SEQUENCE: 42

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
            35                  40                  45

Gly Asp Ile Ile Pro Ser Asn Gly Ala Thr Phe Tyr Asn Gln Lys Phe
        50                  55                  60

Lys Gly Lys Ala Thr Leu Thr Val Asp Arg Ser Ser Ser Thr Ala Tyr
65                  70                  75                  80

Met His Leu Asn Ser Leu Thr Ser Glu Asp Ser Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser
            115
```

<210> SEQ ID NO 43
<211> LENGTH: 113
<212> TYPE: PRT
<213> ORGANISM: mouse

<400> SEQUENCE: 43

```
Asp Phe Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95
```

```
Asp Tyr Ser Tyr Pro Tyr Thr Phe Gly Gly Thr Lys Leu Glu Ile
            100                 105                 110
Lys

<210> SEQ ID NO 44
<211> LENGTH: 10
<212> TYPE: PRT
<213> ORGANISM: Homo sapiens

<400> SEQUENCE: 44

Lys Pro Leu Pro Glu Val Thr Asp Glu Tyr
1               5                   10
```